US007250270B2

(12) United States Patent
Goldrick et al.

(10) Patent No.: US 7,250,270 B2
(45) Date of Patent: Jul. 31, 2007

(54) METHODS AND COMPOSITIONS FOR PREPARING TISSUE SAMPLES FOR RNA EXTRACTION

(75) Inventors: Marianna Goldrick, Austin, TX (US); Juanita C. Gonzales, Austin, TX (US)

(73) Assignee: Ambion, Inc., Austin, TX (US)

( * ) Notice: Subject to any disclaimer, the term of this patent is extended or adjusted under 35 U.S.C. 154(b) by 483 days.

(21) Appl. No.: 10/462,091

(22) Filed: Jun. 13, 2003

(65) Prior Publication Data

US 2004/0253661 A1  Dec. 16, 2004

(51) Int. Cl.
G01N 1/30 (2006.01)
G01N 33/48 (2006.01)

(52) U.S. Cl. .................................... 435/40.5
(58) Field of Classification Search ............... 435/40.5
See application file for complete search history.

(56) References Cited

U.S. PATENT DOCUMENTS

| 5,614,376 | A | 3/1997 | Copley et al. | 435/30 |
| 6,316,234 | B1 | 11/2001 | Bova | 435/173.7 |
| 6,348,325 | B1 * | 2/2002 | Zahniser et al. | 435/40.5 |
| 2002/0006625 | A1 | 1/2002 | Chu | 435/6 |
| 2002/0013222 | A1 | 1/2002 | Rei et al. | 502/200 |
| 2003/0087333 | A1 * | 5/2003 | Hirai et al. | 435/40.5 |

FOREIGN PATENT DOCUMENTS

DE 2409167 8/1975

OTHER PUBLICATIONS

Tanji, N. et al. 2001. Effect of Tissue Processing on the Ability to Recover Nucleic Acid fronm Specific Renal Tissue Compartments by Laser Capture Microdissection. Experimental Nephrology, vol. 9, pp. 229-234.*
"HistoGene™ LCM frozen section staining kit," Arcturus Catalog #KIT0401, Version A, Arcturus Systems for Microgenomics, 2001 copyright date.
"Optimized protocol for preparing and staining LCM samples from frozen tissue and extraction of high-quality RNA," Arcturus Application Note #1, found at the Arcturus website arctur.com/images/pdf/HistoGene_Application_Note.pdf, Aug. 2001.
"RNAqueous™ -Micro Instructional manual," Version 0303, Cat #1927, Ambion, Inc., 2003.
"Staining protocol for LCM samples," Ambion TechNotes found at http://www.ambion.com/techlib/misc/LCM_staining.html, May 6, 2003.
"Working with laser capture microdissection samples," Ambion TechNotes, vol. 9, No. 6, Nov. 2002, found at http://www.ambion.com/techlib/tn/96/9616.html, May 6, 2003.
Fend et al., "Immuno-LCM: laser capture microdissection of immunostained frozen sections for mRNA analysis," *Am. J. Pahtol.*, 154:61-66, 1999.
Fend et al., "Laser capture microdissection: methodical aspects and applications with emphasis on immuno-laser capture microdissection," *Pathobiology*, 68:209-214, 2000.
Fink et al., "Immunostaining and laser-assisted cel picking for mRNA analysis," *Lab. Invest.*, 80:327-333, 2000.
Fink et al., "Immunostaining for cell picking and real-time mRNA quantitation," *Am. J. Pathol.*, 157:1459-1466, 2000.
Goldworthy et al., "Effects of fixation on RNA extraction and amplification from laser capture microdissected tissue," *Molecular Carcinogenesis* 25:86-91, 1999.
Kazumori et al., "Analysis of gastrin receptor gene expression in proliferating cells in the neck zone of gastic fundic glands using laser capture microdissection," *FEBS Letters* 489:208-214, 2001.
Kohda et al., "Analysis of segmental renal gene expression by laser capture microdissection," *Kidney International*, 57:321-331, 2000.
Lindeman et al., "Gene transcript quantitation by real-time RT-PCR in cells selected by immunohistochemistry-laser capture microdissection," *Diagn. Mol. Pathol.*, 11:187-192, 2002.
Luzzi et al., "Expression profiling of ductal carcinomal in situ by laser capture microdissection and high-density oligonucleotide arrays," *Am. J. Pathol.*, 158:2005-2010, 2001.
Murakami et al., "IF-LCM: laser capture microdissection of immunofluorescently defined cells for mRNA analysis rapid communication," *Kidney International*, 58:1346-1353, 2000.
Tanji et al., "Effect of tissue processing on the ability to recover nucleic acid from specific renal tissue compartments by laser capture microdissection," *Exp. Nephrol.*, 9:229-234, 2001.
Trogan et al., "Laser capture microdissection analysis of gene ecpression in macrophages from atherosclerotic lesions of apolipoprotein E-deficient mice," *Proc. Natl. Acad. Sci, USA*, 99:2234-2239, 2002.
Vincent et al., "Analysis of neuronal gene expression with laser capture microdissection ," *J. Neurosci. Res.* 69:578-586, 2002.
Wong et al., "Genetic mosaic analysis based on Cre recombinase and navigated laser capture microdissection," *Proc. Natl. Acad. Sci., USA*, 97:12601-12606, 2000.
Craven et al., "Laser capture microdissection and two-dimmenrsional polyacrylamide gel electrophresis: evaluation of tissue preparation and sample limitations," *Journal of Pathology*, 160(3):815-822, 2002.

* cited by examiner

*Primary Examiner*—Jon Weber
*Assistant Examiner*—Kailash C. Srivastava
(74) *Attorney, Agent, or Firm*—Fulbright & Jaworski LLP

(57) ABSTRACT

The present invention concerns the methods and compositions for preparing a tissue section or biological sample, particularly to preserve RNA in the section or sample, by not exposing or contacting the sample or section to a solution that is composed of mostly water. Tissue sections can be fixed, stained, and dehydrated for subsequent manipulation, including laser capture microdissection (LCM) for further analysis using methods and/or compositions of the invention.

21 Claims, 14 Drawing Sheets

METHODS AND COMPOSITIONS FOR PREPARING TISSUE SAMPLES FOR RNA EXTRACTION

The government may own rights in the present invention pursuant to grant number R43-CA88699 from National Institutes of Health/National Cancer Institute.

BACKGROUND OF THE INVENTION

1. Field of the Invention

The present invention relates generally to the fields of histology and molecular biology. More particularly, it concerns compositions and methods for preparing a tissue section that allows RNA in the section to be recovered more abundantly and in a more intact form than previous methods in which significant degradation occurred.

2. Description of Related Art

Histological staining of thin tissue sections mounted on slides is frequently used to improve the ability to distinguish specific subregions and cellular structures during microscopic examination. Different stains, optimized for visualization of different structures in different types of tissue, for example liver, brain, kidney, tumor biopsies, etc. are used by pathologists and researchers for specific applications, for example diagnosis of metastatic disease based on abnormal tissue morphology.

In addition to microscopic examination, molecular tests are increasingly being carried out on thin tissue sections in order to provide additional information about the sample, including detection of mutations and assessment of patterns of gene expression. Molecular tests require extraction of nucleic acid, i.e., DNA and RNA, from the sectioned tissue.

Molecular tests based on RNA analysis provide information about the expression of genes in the tissue sample, for example quantitative reverse transcription-polymerase chain reaction (qRT-PCR) is one type of molecular assay that is used to determine whether and to what extent given genes are expressed in a tissue sample. Microarray expression profiling is another example of an RNA-based molecular test that can be used to determine which subset of genes are expressed in a specific tissue sample.

RNA is a particularly labile biomolecule, being much more susceptible to degradation by endogenous and exogenous nucleases and to nonspecific degradation by divalent cations, heat, and elevations in pH, compared to DNA. Extraction of RNA from tissue sections in an intact form is required for subsequent T7 RNA polymerase-mediated linear amplification using various strategies (ref Eberwine patents and papers). Linear amplification is generally required for microarray analysis on thin tissue sections, since the amount of RNA needed for conversion to cDNA in order to carry out microarray hybridization is several micrograms, and this amount of RNA cannot generally be obtained from this type of sample.

Treatment of tissue with aldehyde fixatives such as formalin and paraformaldehyde causes chemical crosslinking of nucleic acid, which compromises the ability to extract intact RNA and/or to carry out reverse transcription using RNA from the fixed samples. For this reason, the alternative processing method using frozen tissue, rather than aldehyde-fixed tissue, is recommended in cases where the RNA will be extracted for molecular tests, especially for microarray expression profiling. Successful extraction of intact RNA from frozen sections is however also challenging, because the endogenous nucleases in the tissue, especially ribonucleases, must be maintained in an inactive form during the isolation process. Whereas aldehyde-based fixatives generally result in irreversible inactivation of endogenous RNases (due to chemical crosslinking), the alternative tissue processing method, i.e., using frozen tissue, does not render endogenous ribonucleases permanently inactive. When the tissue is thawed, RNases generally become active. Endogenous RNase activity can result in partial or complete degradation of the tissue RNA, rendering it useless for molecular tests.

Methods used to inactivate endogenous RNases during sample processing include addition of placental RNase inhibitor to the reagents used for fixing and staining the tissue, and minimizing the time in which the tissue sections are exposed to aqueous environments. It is recognized that placing the tissue sections in aqueous solutions provides an opportunity for the endogenous RNases, which are inactive while in the frozen state, to become re-activated and degrade the cellular RNA.

However, protocols for fixing and staining frozen tissue sections generally include 3 main steps in which the sections are placed in aqueous solution (i.e., water). The steps commonly used to stain and process frozen tissue for histological examination are summarized as follows:

1. Sections are cut on a cryostat and transferred from the cryostat blade to clean glass microscope slides, where they are allowed to partially thaw for a few seconds in order to facilitate their adherence to the glass surface of the slide.
2. Sections mounted on slides are then "fixed" by submerging the slides successively into solutions of "graded ethanols". Typically the graded ethanol series includes an initial submersion in 100% or 95% ethanol, followed by successive submersions in 75% or 70% ethanol, and finally in 50% ethanol. The suggested length of time in which the tissue is kept in each solution generally ranges from a few seconds to a few minutes.
3. After the graded ethanol series, the fixed tissue section is submerged in water for a period of several seconds to several minutes.
4. The tissue section is then submerged in the stain solution for a period of several seconds to several minutes. Examples of common histological stains are hematoxylin, eosin, and cresyl violet. The stains are typically either purchased as ready-to-use aqueous solutions, or are prepared by dissolving powdered stains in water.
5. The stained sections are then typically briefly submerged in water to remove excess stain. In some cases the sections may be stained with a second stain ("counter-stained") to improve the ability to visualize certain cellular substructures.
6. The sections are then typically submerged in a second series of graded ethanol solutions of increasing ethanol concentration, for example, they may be placed sequentially into solutions of 50% ethanol, 70-75% ethanol, 95% ethanol, and 100% ethanol. This series serves to dehydrate the tissue section.
7. Certain applications such as laser capture microdissection (LCM, described in detail below), require that the stained sections be completely dry. To achieve this, the sections are transferred from 100% ethanol into xylene and in some cases followed by transferring to a second solution of xylene, in order to remove all residual ethanol from the section.

A feature of many, if not all, of the published protocols for processing tissue is that they specify several steps in which the slides are dipped in water and aqueous staining solutions (see e.g., Kohda et al., 2000; Wong et al., 2000; Kazumori et al., 2001; Luzzi et al., 2001; Tanji et al., 2001). One paper stated that exposure to aqueous solutions destroys 99% of the mRNA (Murakami et al., 2000). The consensus from the literature is that RNA quality is improved in LCM samples by minimizing the time in which the tissue is exposed to aqueous environments, leading to recommendations that staining and destaining steps be reduced from minutes to seconds (Goldsworthy et al., 1999; Kohda et al., 2000; Kazumori et al., 2001; Tanji et al., 2001). However, RNA quality was not always improved simply by reducing the time the tissue sections were incubated in aqueous solutions.

Existing protocols continue to involve steps in which tissue samples are exposed to aqueous environments in which RNA can be degraded. Therefore, there is still a need for improved methods and compositions for preparing samples with RNA remaining intact.

SUMMARY OF THE INVENTION

The present inventions are based on the observations that 1) RNA isolated from sections using published procedures is degraded; 2) RNA degradation is due to endogenous RNases; and, 3) eliminating exposure to water improves RNA quality. Therefore, the present invention concerns compositions and methods for preparing a biological sample in order to maintain its integrity, particularly for subsequent evaluation and characterization. In many embodiments of the invention, maintaining the integrity of specific structures, macromolecules, and parts of the sample is desired. In some embodiments, preservation of nucleic acids such as RNA and/or DNA can be achieved using methods and compositions of the invention for preparing a biological sample. In certain embodiments, the biological sample includes tissue that has been sectioned ("tissue section," which has its ordinary and plain meaning). A tissue section is commonly placed on slide.

The present invention concerns methods for preparing a tissue section or other biological sample by preparing the section or sample in the absence of a solution that is 100% water (v/v). The term "water" includes, but is not limited to, distilled water, deionized water, deionized distilled water (ddH$_2$O), and diethyl pyrocarbonate (DEPC)-treated water.

In some embodiments of the invention, methods include a) contacting a tissue section with a first set of one or more solutions comprising no more than about 50% water; b) contacting the tissue section with a stain in a solution comprising no more than about 50% water; c) then contacting the tissue section with a second set of one or more solutions comprising no more than about 50% water, wherein the tissue section is not contacted with a solution that is more than about 50% water. The term "contacting" is used according to their plain and ordinary meaning to refer to exposing or submerging of the tissue section to or in a solution. "Dipping" the sample or section into a solution and incubating the sample or section in the solution are ways of contacting the sample or section with the solution. It will be further understood that a solution may have a particular concentration of components, which may be altered once the sample is placed in the solution or the solution is contacted with the sample, because the sample itself has some components, such as carryover from the previous solution. Accordingly, the concentration of the components in the solution is understood to refer to the amount of those components just prior to the solution's contacting the sample. In some embodiments of the invention, slides are tapped on an absorbent surface to minimize carryover or contamination.

In other embodiments, methods include a) contacting a tissue section with a first set of one or more solutions comprising alcohol; b) contacting the tissue section with a stain in a solution comprising an organic solvent; c) contacting the tissue section with a second set of one or more solutions comprising alcohol, wherein the tissue section is not contacted with a solution that does not comprise alcohol or an organic solvent.

Steps taken before the sample is exposed to a stain are pre-staining steps, while those taken after exposure to a stain are post-staining steps. Prior to or after staining, the sample or section can be exposed to a set of solutions, wherein "set of solutions" refers to one or more solutions.

The solutions may contain, have, be constituted of, or be a certain percentage of a particular compound. These terms are used interchangeably herein to refer to concentrations. It is contemplated that solutions of the invention may be about, less than about, or more than about 5, 10, 15, 20, 25, 30, 35, 40, 45, 50, 55, 60, 65, 70, 75, 80, 85, 90, 95, or 100% water. Any articulated concentration does not mean the solution contains only that component specified; instead, solutions may contain other components as well, with the concentration of the specified component. Unless otherwise specified, percentages of a liquid in a solution refer to percentage volumes (v/v). In specific embodiments, the tissue section is not contacted with a solution that is more than about 80%, 90% or 100% water. Moreover, in specific embodiments, the solution containing the stain (alternatively referred to as "stain solution") is less than about 10, 9, 8, 7, 6, 5, 4, 3, 2, 1% water. It is contemplated that the stain solution does not contain any water in some embodiments. Moreover, the stain solution contemplated as part of the invention is a solution in which RNase activity is reduced, substantially reduced, or eliminated. It is contemplated that the term "reduced" means that RNase activity in the solution is reduced by at least about 20, 25, 30, 25, 40, 45, 50, 55, 60, 65, 70, 75, 80, 85, 90, 95% or more relative to RNase activity in a solution that is 100% water. The term "substantially reduced" means the activity is reduced by at least about 70, 75, 80, 85, 90, 95% or more relative to RNase activity in a solution that is 100% water. The term "eliminated" means that RNA activity in the solution is less than about 5% the activity relative to RNase activity in a solution that is 100% water. RNA activity can be measure, for example, using Northern blot analysis or chromatographs showing RNA quantity and/or quality.

Stains contemplated for use with the invention include, but are not limited to, any stain selected from the group consisting of cresyl violet acetate, cresol red, cresol purple, acid fuchsin, acridine orange, alizarin red ("mordant red 3"), pyronin B, orcein, Giemsa stain, gallocyanine, hematoxylin, and eosin.(see Floyd J. Green, The Sigma Aldrich Handbook of Stains, Dyes, and Indicators, Aldrich Chemical Company, Inc., Milwaukee, Wis., 1990, which is hereby incorporated by reference). In some embodiments, a sample is exposed to 1, 2, 3, 4, 5 or more stains either at the same time or sequentially (one after the other). Thus, in some embodiments, a sample or section is exposed to both hematoxylin and eosin (H & E stain). The term "dye" is used interchangeably with the term "stain."

Solutions of the invention may be, be at least, or be at most about 5, 10, 15, 20, 25, 30, 35, 40, 45, 50, 55, 60, 65, 70, 75, 80, 85, 90, 95, or 100% alcohol. Alcohols, though not limited to the following, may be selected from the group consisting of ethanol, methanol, and propanol. Moreover, one or more alcohols may be mixed together and used in methods and compositions of the invention.

It is contemplated that one, two, three, four, five, six, seven, eight, nine, ten or more solutions to which the sample exposed or incubated in may contain the above-described percentages of components. Moreover, all of the solutions to which the sample is exposed can contain above a certain percentage of an organic solvent, such as alcohol, or contain below a certain percentage of water.

Moreover, solutions used in methods and compositions of the invention may include a certain percentage of water and an organic solvent. Alcohol is an organic solvent, and, as discussed above, can be a component of solutions of the invention in some embodiments. In other embodiments, a solution may contain a non-alcohol organic solvent, meaning the solution contains an organic solvent that is not an alcohol. Organic solvents and non-alcohol organic solvents may be, be at least, or be at most about 5, 10, 15, 20, 25, 30, 35, 40, 45, 50, 55, 60, 65, 70, 75, 80, 85, 90, 95, or 100% organic solvent. The present invention covers, but is not limited to, a non-alcohol organic solvent that is a hydrocarbon selected from the group consisting of xylene or toluene. Thus, in some embodiments of the invention, a section is exposed to xylene.

Other steps that may be included in methods of the invention are performing laser capture microdissection (LCM) on the sample or section and/or extracting nucleic acid molecules from it. In some embodiments, LCM is first performed and then nucleic acids are extracted or isolated. In specific embodiments, the nucleic acid molecule is RNA, which can be mRNA, rRNA, tRNA, microRNA, or any combination thereof.

Slides may be used immediately or stored desiccated for some time before LCM or extraction procedures. Slides may be stored for at least, at most, or about 1, 2, 3, 4, 5, 6, 7, 8, 9, 10, 11, 12, 13, 14, 15, 16, 17, 18, 19, 20, 21, 22, 23, 24 hours or more, and 1, 2, 3, 4, 5, 6, 7 or more days, and 1, 2, 3, 4, 5 or more weeks, and 1, 2, 3, 4, 5, 6, 7, 8, 9, 10, 11, 12 or more months.

The present invention specifically includes methods for preparing a tissue section for RNA extraction comprising: a) contacting the tissue section with a first solution that is at least about 70% alcohol; b) exposing the tissue section to second solution comprising a stain and at least about 90% alcohol; c) contacting the tissue section with a third solution that is at least about 70% alcohol; d) contacting the tissue section with a fourth solution that is at least about 95% alcohol; e) contacting the tissue section with a fifth solution that is about 100% alcohol; f) contacting the tissue section with a sixth solution comprising xylene; and, g) extracting RNA from the tissue section. It is contemplated that a subset of these steps or additional steps may be used in other methods of the invention.

The invention also concerns compositions and kits. Any of the solutions described above is contemplated as part of the invention. A solution lacking water but comprising a dye or stain is specifically included as part of the invention.

Kits are also contemplated as part of the invention. In some embodiments, there are kits for preparing a tissue section comprising, in suitable container means: a) a series of dehydrating solutions comprising an alcohol, wherein any water in the solutions has been treated with DEPC; b) a stain solution comprising a stain dissolved in an organic-solvent containing solution. A series of solutions refers to multiple solutions with different concentrations of similar or the same components. In specific embodiments, the series of dehydrating solutions comprises at least a first solution having at least about 70% alcohol, a second solution having at least about 95% alcohol, and a third solution having about 100% alcohol. The kit may include one or more non-alcohol organic solutions, such as a xylene solution.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or." Throughout this application, the term "about" is used to indicate that a value includes the standard deviation of error for the device or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1C is scaled for maximum sensitivity; all other panels are on the same scale. Note that the RNA is intact in sectioned tissue prior to processing (FIG. 1A) and after processing when aqueous pre-staining, staining, and post-staining steps are omitted (FIG. 1E).

DESCRIPTION OF ILLUSTRATIVE EMBODIMENTS

Figure 1A:
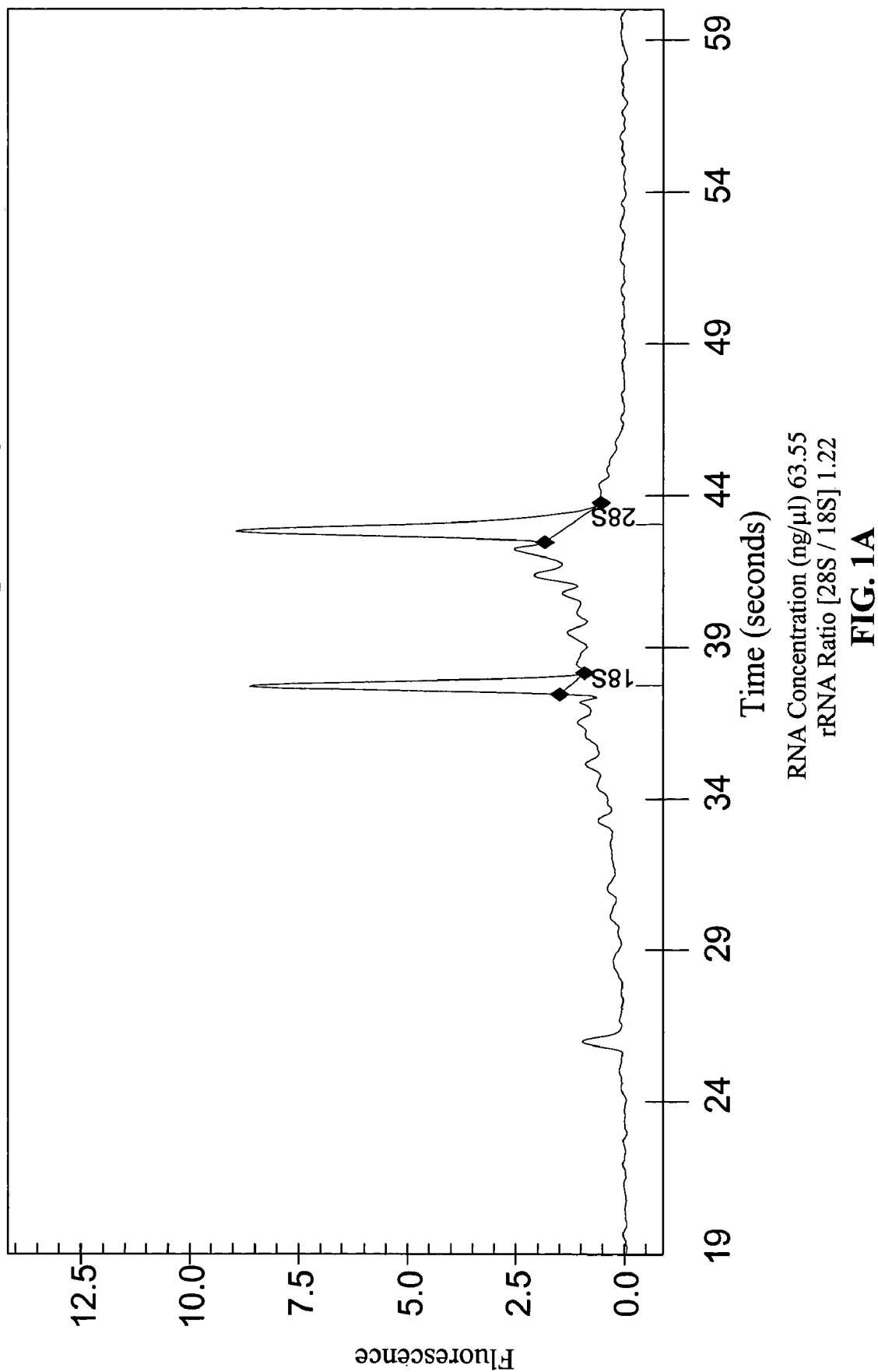
FIGS. 1A-F. Degradation of RNA after exposure to aqueous staining. Mouse brain sections were processed as described in the text and analyzed on the Agilent Bioanalyzer. RNA degradation in FIGS. 1B-D is indicated by the absence of the characteristic 18S and 28S ribosomal RNA peaks.
Figure 1B:
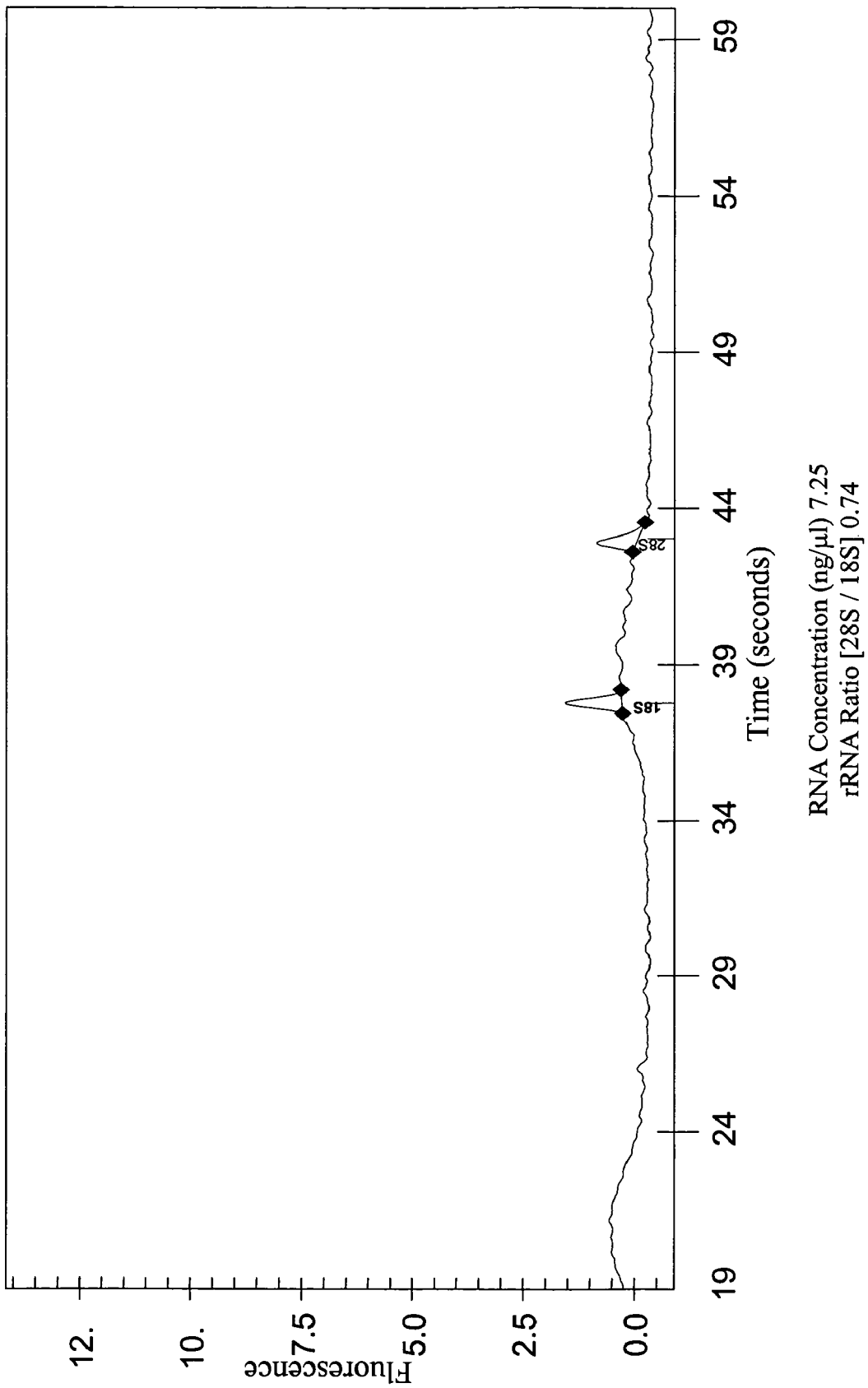
Figure 1C:
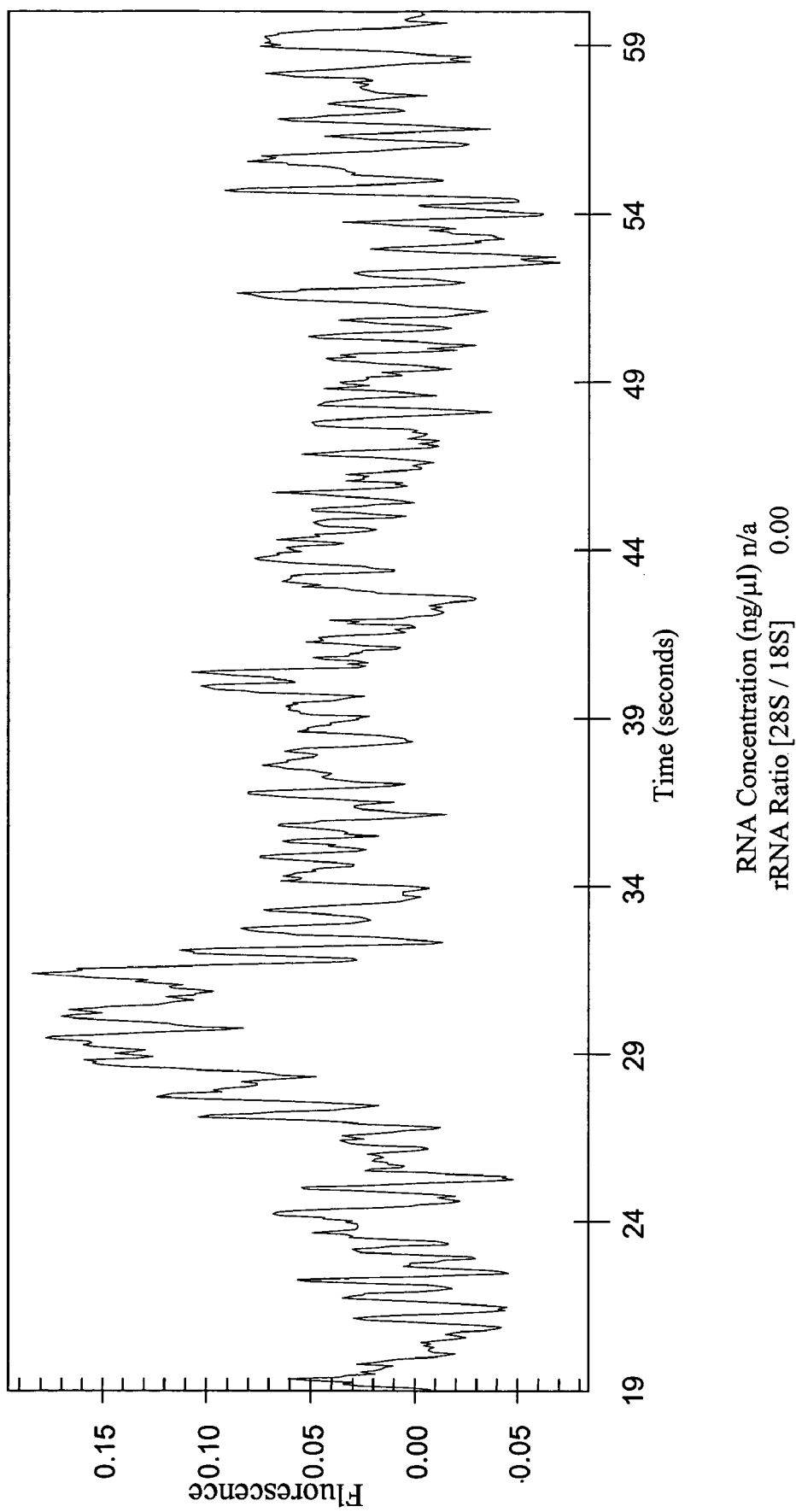
Figure 1D:
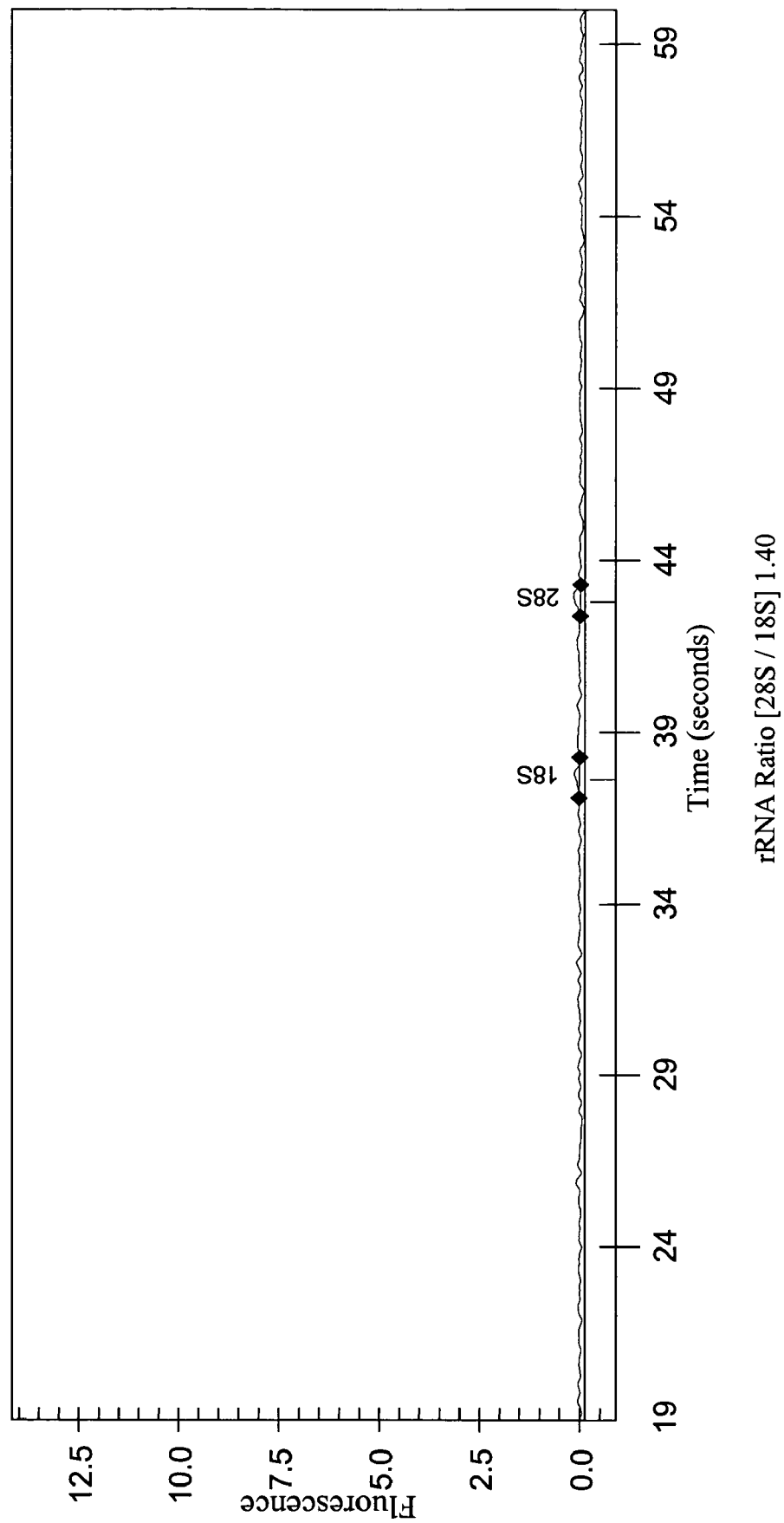
Figure 1E:
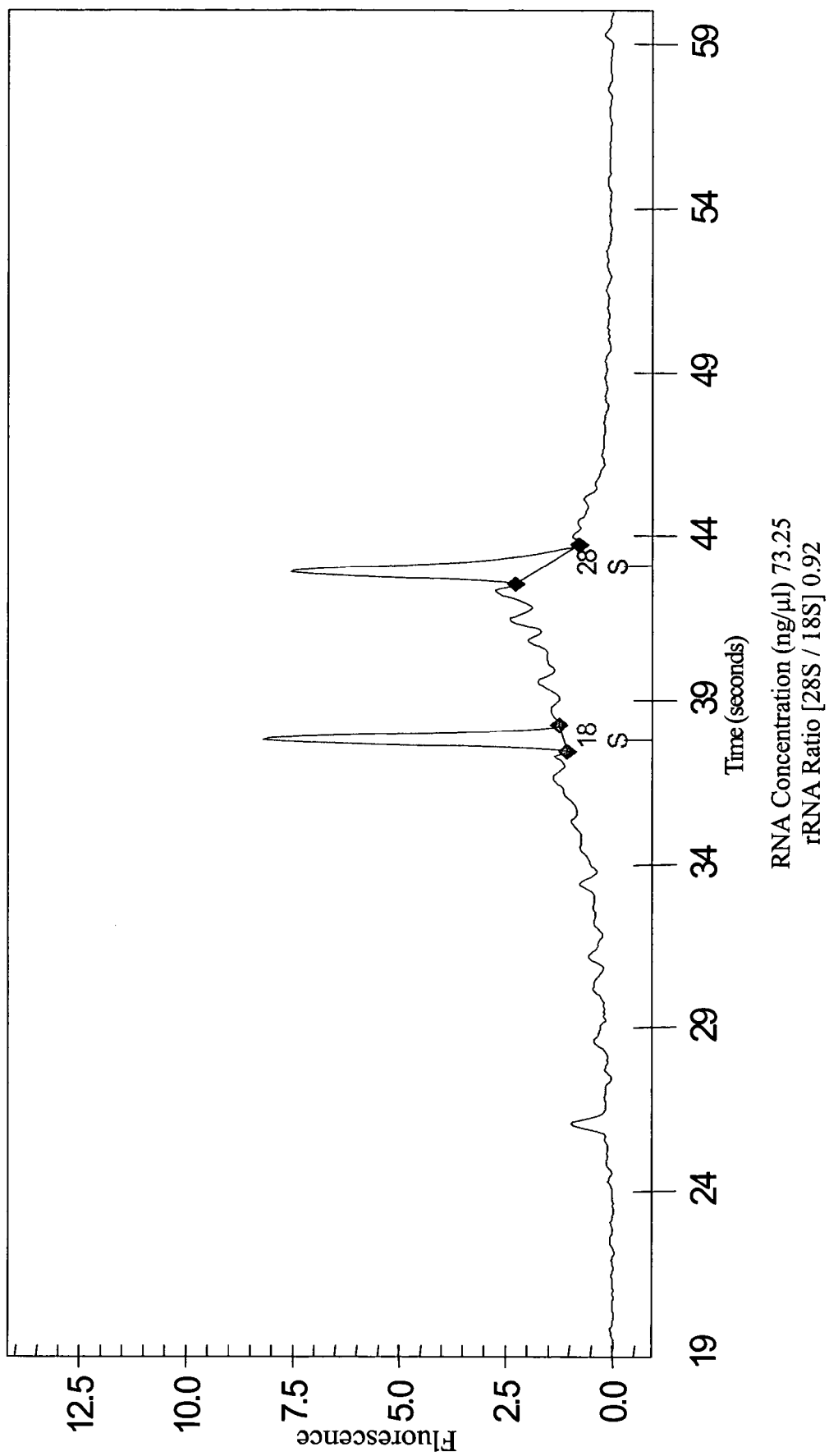
Figure 1F:
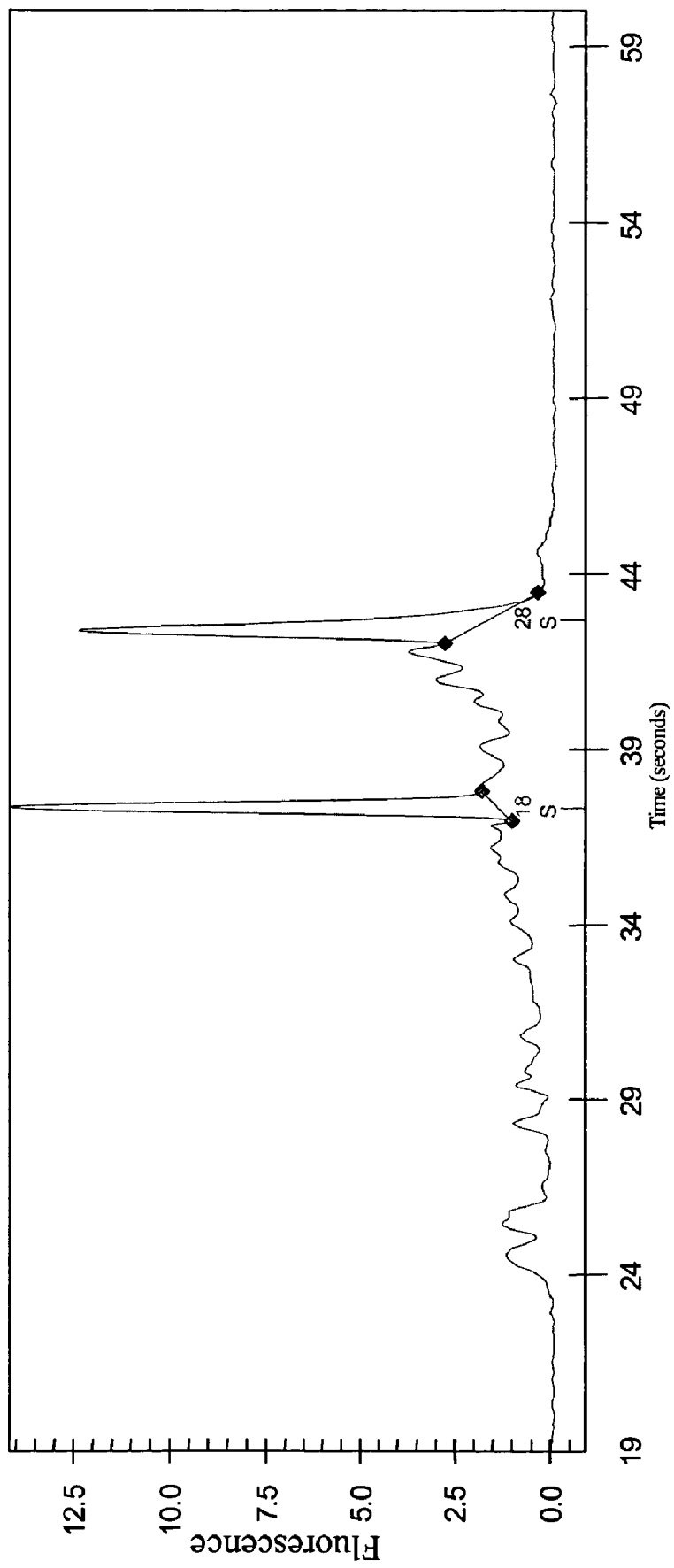

The present invention concerns compositions and methods for preparing a tissue section or sample in order to preserve the nucleic acids, particularly RNA, in the sample. The preparation of the biological sample can include sectioning, fixing, staining, additional fixing, washing, dehydrating, extracting or isolating nucleic acids, inactivating proteins—including nucleases, microdissecting, and/or amplifying nucleic acids. Many of these steps are discussed in further detail.

I. Preparation of Samples

A. Tissue Embedding and Sectioning

Solid tissues of various types are typically prepared for microscopic examination by treating them in such a way that they can be cut into thin pieces of ~3-20 microns in thickness (a process referred to as "sectioning" the tissue) and mounted onto glass microscope slides for visualization of cellular structure. In order to impart rigidity to the tissue to permit it to be sectioned, the tissue is typically treated in one of two ways prior to being cut: either the tissue is fixed in a reagent such as formalin or paraformaldehyde and subsequently embedded in paraffin, or the tissue is "snap-frozen", for example by placing it into liquid nitrogen or in a dry ice-ethanol bath, and then embedded with a compound called OCT (which stands for Optimal Cutting Temperature).

The processes of embedding and section are well known to those of skill in the art and can be readily found in the following references, Fawcett, 1994; Leeson, 1988; Rogers, 1983; the Arcuturus Application Note (found on the world wide web at arctur.com/images/pdf/HistoGene_Application_Note.pdf); U.S. Pat. Nos. 5,614,376 and 6,316,234, U.S. Patent Publication No. 20020006625, all of which are hereby incorporated by reference in their entirety.

B. Staining

Many common histological stains, including hematoxylin, eosin B and cosin Y, toluidine blue, and cresyl violet acetate, are soluble in 100% ethanol at levels between 10-30 mg/ml (Sigma-Aldrich Handbook of Stains, Dyes, and Indicators). These dyes are typically provided as a powder and then dissolved in a solution containing water, usually only water. However, in the context of the present invention, such dyes can be dissolved in a solution containing an organic solvent as well. Organic solvents that may be used include alcohols such as ethanol, methanol, propanol, isopropanol, and any other solvent in which the dye dissolves.

C. Pre-Staining and Post-Staining

Pre-staining and post-staining steps are generally implemented to fix the sample prior to staining and then to de-stain or dehydrate it after it has been stained. Thus, the sample may be exposed to any compound that achieves these results. Solutions typically used include organic solvents.

Organic solvents include hydrocarbons (examples include n-pentane, n-Hexane, n-Heptane, n-Octane, n-Nonane, n-Decane, 2,2,4-Trimethyl Pentane, Cyclohexane, Benzene, Toluene, Ethylbenzens, Xylene (Mixed Isomers), C9 Aromatics, and Tetralin); alcohols (examples include Methanol, Ethanol, n-Propanol, i-Propanol, n-Butanol, 1-Butanol, s-Butanol, n-Amyl Alcohol, i-Amyl Alcohol, Cyclohexanol, n-Octanol, Ethanediol, Diethylene Glycol, and 1,2-Propanediol); glycol ethers (examples include Propylene Glycol Methyl Ether, Ethylene Glycol Methyl Ether, Ethylene Glocol Ethyl Ether, and Ethylene Glycol Monobutyl Ether);

chlorinated solvents (examples include Methylene Chloride, Chloroform, Carbon Tetrachloride, 1,2-Dichloroethane, 1,1, 1-Trichloroethane, Trichloroethylene, Perchloroethylene, and Monochlorobenzene); ketones (examples include Acetone, Methyl Ethyl Ketone, Methyl Isobutyl Ketone, Cyclohexanone, n-Methyl-2-Pyrrolidone, Acetophenone); ethers (examples include Diethyl Ether, Diisopropyl Ether, Dibutyl Ether, Methyl Tert Butyl Ether, 1,4-Dioxane, and Tetrahydrofuran); esters (Methyl Acetate, Ethyl Acetate, Isopropyl Acetate, n-Butyl Acetate, and Cellosolve Acetate); and miscellaneous solvents (examples include Dimethylformamide, Dimethylacetamide, Dimethylsulphoxide, Sulfolane, Carbon Disulphide, Acetic Acid, Aniline, Nitrobenzene, Morpholine, Pyridine, 2-Nitropropane, Acetonitrile, Furfuraldehyde, Phenol, and Water). Any of these may be used in methods and compositions of the invention to the extent they do not compromise the integrity of that part of the sample which is of interest, such as the RNA, in some embodiments of the invention. Furthermore, preferred organic solvents are those that promote methods of the invention, that is, maintaining the integrity of the sample and allowing the sample to be analyzed or portions of the sample to be isolated, characterized, or evaluated. Thus, it is clear that in certain embodiments, a dye can be dissolved in the organic solvent or a solution comprising the organic solvent. Moreover, solvents that are combinable may be combined in some embodiments of the invention.

Other methods and compositions that may be used in the context of this invention are well known, including examples disclosed in U.S. Patent Application No. 20030064518, which is hereby incorporated by reference in its entirety.

D. Laser Capture Microdissection (LCM)

RNA-based molecular studies typically aim to determine the subset of genes that are expressed as mRNA in a tissue sample, and/or to quantify the level of particular mRNAs in the sample. In order to derive meaningful information about the mRNA expression patterns in a tissue sample, it is desirable to carry out the analysis on pure populations of cells obtained from the sample. Most mammalian tissues are comprised of a variety of different cell types and structures, for example the mammalian brain contains neurons, glial cells, and endothelial cells, the proportions of which vary widely among different anatomic regions; kidney tissue sections include a variety of structures such as ascending and descending microtubules and glomeruli; and tumor biopsies, even small samples such as fine-needle aspirates, are composed of stromal cells, inflammatory cells, and blood vessels, in addition to malignant cells. Techniques for obtaining homogeneous populations of specific cells and/or structures to use for molecular studies include use of micropipets and micromanipulators to separate and recover cells of interest, and more recently, the technique of laser capture microdissection (LCM) and other laser-assisted microdissection methods. LCM is an attractive method for obtaining pure populations of cells because it is relatively rapid and non-labor-intensive, and can be performed by users with a minimum of training. LCM was developed under a cooperative research and development agreement (CRADA) between the National Institute of Health/National Cancer Institute, and Arcturus Instruments, Inc.

Briefly, LCM as it is applied to RNA-based molecular studies involves preparation and staining of frozen tissue sections as outlined above, including complete dehydration of the stained sections in 100% ethanol followed by complete removal of ethanol by treating the tissue with xylene. The processed tissue sections are then examined under a light microscope. Regions of interest are visualized through a thermoplastic ethylene vinyl acetate film containing a near-infrared-absorbing dye, which is attached to the bottom of a clear microfuge tube cap (~6 mm in diameter). A laser pulse with a diameter of ~10-600 microns (typically ~30 um) with a wavelength matched to the infrared dye is then directed onto the cells of interest through the film. The laser energy is absorbed by the dye in the film, which causes the film to melt and flow onto the targeted area, where it cools and bonds with the underlying cell(s). The film is then lifted, along with the adhered cell or clusters of cells. Proteins and nucleic acids are not degraded by the laser due to the short duration (~50 ms) of the pulse. Captured cells can be used for analyzing enzymes or peptides in proteomics experiments, as well as for mRNA expression studies.

Isolation of RNA from LCM-captured cells is the first step in the post-capture "molecular biology" phase of the experiment. The number of cells captured for use in a single experiment is generally on the order of 100-10,000, depending on the frequency of the target cells and on whether single cells, cell clusters, or specific structures are captured. Analysis of RNA from LCM samples requires that the RNA be recovered as completely as possible. In addition, for use in microarray experiments, the RNA needs to be intact, because only intact RNA can serve as substrate for subsequent T7-mediated amplification (Fend et al., 2001). It was expected that recovery of intact RNA might be especially challenging from LCM samples, and we have found this to be the case. The fairly extensive front-end manipulation used to prepare the tissue (embedding, fixing, sectioning, staining/destaining, and dehydrating) offer the opportunity for intracellular RNA degradation. Of the two main ways to fix, embed, and section solid tissue, namely formalin fixation followed by paraffin embedding and sectioning at room temperature, or alternatively, snap-freezing and OCT embedding followed by cryostat sectioning at approximately –25° C., the latter procedure is generally used for tissue from which RNA will be recovered. This is because formalin cross-links nucleic acids and compromises their use as substrates for downstream enzymatic reactions (reverse transcription and PCR). However, cryo-processing methods are also problematic for RNA recovery because they do not inactivate endogenous nucleases in the sample.

Other components and methods that may be used to implement embodiments of the invention are described in U.S. Patent Publication No. 20020132222, which are hereby incorporated by reference in their entirety.

II. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

RNA Isolated from Tissue Sections Processed Using Published Procedures is Degraded The effect of the various steps used to prepare tissue samples for LCM, and of the LCM process itself, on the yields and quality of RNA recovered was systematically investigated. Protocols described in the literature were used to process various mouse tissues and human tissues were obtained from the Co-operative Human Tissue Network (CHTN) and used to study the effects. The steps used to prepare frozen tissues for LCM and subsequent RNA recovery can be divided into four stages: 1) embedding and sectioning; 2) pre-staining fixation and hydration; 3) staining; and 4) post-staining processing and dehydration. The protocol recommended by Arcturus, Inc. for carrying out these steps is described in a technical bulletin, "Optimized Protocol for Preparing and Staining LCM Samples from Frozen Tissue and Extraction of High-Quality RNA" (found on the world wide web at arctur.com/images/pdf/HistoGene_Application_Note.pdf). Briefly, the steps consist of embedding the snap-frozen tissue in OCT matrix ("Optimal Cutting Temperature," a proprietary polymer that imparts rigidity to the tissue), sectioning the embedded tissue at −25° C. in a cryostat, transferring the cut sections to microscope slides, and dipping the slides sequentially in 75% ethanol and then water for 30 seconds. These pre-stain processing steps are used to fix the tissue, dissolve the OCT, and equilibrate the tissue into the aqueous stain solution. This is followed by staining the sections for 20 seconds, then sequentially dipping them again (30 seconds in each solution) in water, 75% ethanol, 95% ethanol, 100% ethanol, and then in xylene for 5 minutes. A somewhat different protocol is described by Goldsworthy et al. ("Effects of Fixation on RNA Extraction and Amplification from Laser Capture Microdissected Tissue", 1999). This group recommends fixing the cut frozen sections in 70% ethanol followed by hydration in distilled water, staining in Mayer's hematoxylin, rinsing in water, dehydrating in 70% and then 95% ethanol, counterstaining in eosin, clearing the slides twice in 95% ethanol, dehydrating in 100% ethanol, then dipping twice in xylene for 2 minutes.

Analysis of RNA recovered from the stained sections prepared according to techniques involving solutions with 100% water was degraded. This is shown in a Northern blot, by the weak signal of low molecular weight material from replicate LCM-captured human kidney, prostate, colon, and breast tumor samples. To determine the steps at which RNA degradation occurred, RNA was isolated directly from sections on slides after each of the 4 processing stages described above. The RNA was intact in samples after embedding and sectioning, but progressive deterioration of the RNA was observed after stages 2, 3, and 4. Intact RNA could be recovered if the sectioned tissue was processed through the graded ethanol series and xylene, without staining. FIGS. 1A-F shows representative results.

Example 2

RNA Degradation is Not Due to RNase in Solutions and Surfaces

Since RNA degradation was observed in stained tissue, it was investigated whether this was due to RNase contamination of the reagents used. Histological stains such as hematoxylin/eosin, cresyl violet, and toluidine blue are typically made by dissolving powdered stains in water or in phosphate buffer. To rule out RNase contamination of the reagents used to make the stains, synthetic radiolabeled RNA transcripts were incubated for six hours with distilled water and with aqueous solutions of several histological stains, and then analyzed the transcripts on denaturing polyacrylamide gels. The stains tested included commercially available premixed solutions of eosin Y, Harris hematoxylin, and bluing reagent (ThermoShanndon Rapid-Chrome Frozen Section Staining kit) and powdered stains including toluidine blue, cresyl violet, and hematoxylin (EM Science, Sigma and Aldrich). These experiments showed that the RNA degradation observed in stained tissue sections could not usually be attributed to the water or the stain itself, since exposure of radiolabeled transcripts to these reagents did not result in their degradation. An exception was the bluing reagent (used as counterstain in some protocols), but this was an isolated case. The assay was also run on the glass microscope slides and on the thermoplastic film used for LCM (by incubating radiolabeled probe on these surfaces and then running it on a PAGE gel). No degradation of the RNA probe was seen after exposure to these surfaces.

The conclusion from the experiments described above was that the source of RNA degradation usually observed in stained sections was not contamination of the reagents or surfaces in contact with the sample, but was instead due to endogenous RNase in the tissue itself. Evidently the RNase was held in check as long as the tissue was frozen and not exposed to an aqueous environment, but the RNase was reactivated when the tissue was exposed to aqueous conditions.

Example 3

Optimization of Pre-Staining Steps

Whether the 50% and 75% ethanol pre-staining steps could be eliminated was tested. Omitting these ethanol steps and incubating the sections in 95% ethanol directly before staining resulted in extremely poor tissue morphology, in fact it was impossible to bring the stained sample into sharp focus. The water component of the 50% and 75% ethanol solutions is probably required to dissolve the OCT embedding matrix which otherwise interferes with visualizing the tissue.

Example 4

Processing of Mouse Brain Tissue for LCM

The following experiment was performed using sections of mouse brain tissue for LCM. Freshly dissected tissue was rinsed briefly in PBS, then placed into a solution of 30% sucrose in PBS and stored at 4° C. for at least 4 hours, usually with intermittent gentle agitation. Tissue was then embedded in OCT, frozen in dry ice-ethanol, and 10 micron sections cut at −25° C. The tissue was then subject to Pre-staining fixation steps: a) 95% EtOH; b) 75% EtOH; c) 50% EtOH. It was then stained by dipping the slide for 20 seconds in 1% cresyl violet acetate made in 100% EtOH. The slides then underwent post-staining steps by exposure to the following: a) 50% EtOH; b) 75% EtOH; c) 95% EtOH; d) 100% EtOH (30 seconds); e) xylene, 5 minutes; f) repeat xylene, 5 minutes; g) air-dried for approximately 10 minutes. For all post-sectioning steps, the tissue section was quickly dipped 5-7 times in the indicated solution unless otherwise indicated; and, all solutions were made in nuclease-free water.

Slides were then used immediately or stored desiccated for up to several days before LCM. Using this protocol, the yield and intactness of RNA did not decrease significantly during processing, indicating that high-quality RNA can be isolated from sections and LCM samples that were processed using this procedure.

Example 5

Comparison of RNA Isolation Techniques

In these initial studies two different general methods for RNA isolation were used. In both methods, samples were lysed in chaotropic solutions, followed by either phenol/chloroform extraction and alcohol precipitation, or by "solid phase extraction", i.e., binding the RNA to a silica matrix, washing it to remove proteins and DNA, and eluting the RNA from the matrix. Of the samples recovered using solid-phase extraction, some were purified using the reagents (lysis/binding and wash solutions) currently in Ambion's RNAqueous™ kit, some were purified using other commercially available solutions, and some were purified using reagents whose compositions were modified from those in the RNAqueous™ kit. The initial solid-phase extraction experiments used devices with silica filters that were about 9 mm in diameter, while later experiments used smaller filters. Filter size is important because it determines the minimum practical volume of solution needed to elute the RNA. For recovering minute amounts of RNA, lower elution volumes are beneficial because they allow the entire RNA sample to be used as input material in enzymatic reactions, without the need for subsequent concentration adjustments.

Figure 2A:
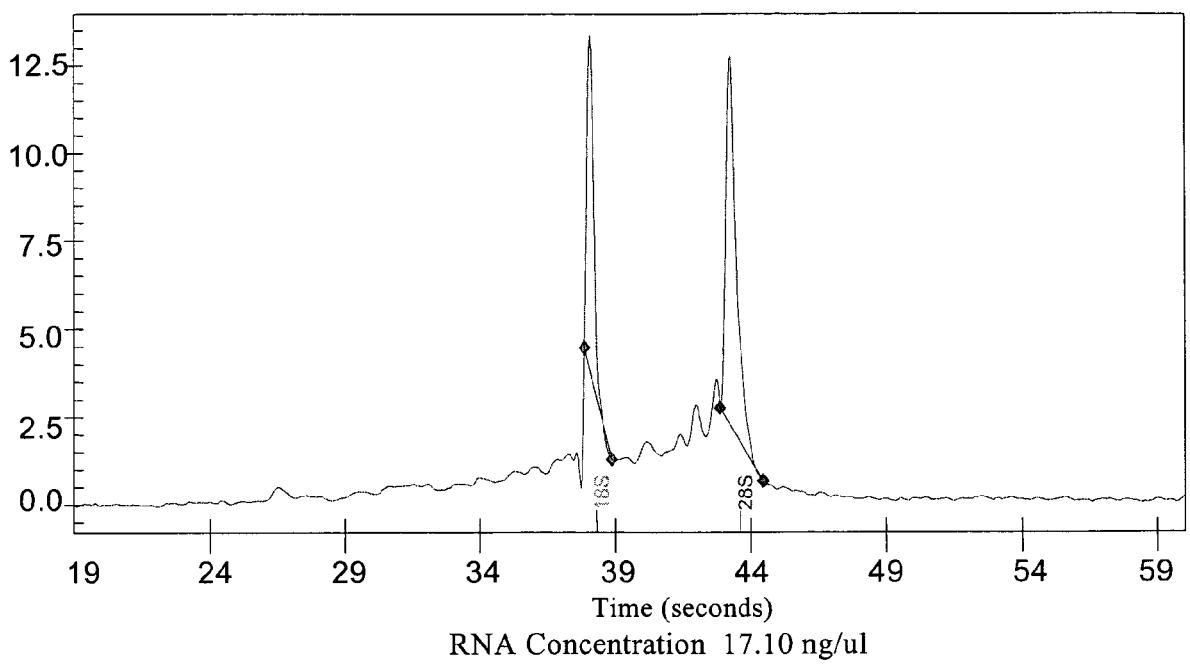
FIGS. 2A-B. Recovery of RNA from processed sections after first and second elutions, using commercially available solid-phase extraction devices. Mouse brain sections were processed and RNA isolated as described in the text. In the accompanying example, approximately 75% of the RNA was recovered after the first elution. Note the Y-axis is drawn to the same scale in the two panels.
Figure 2B:
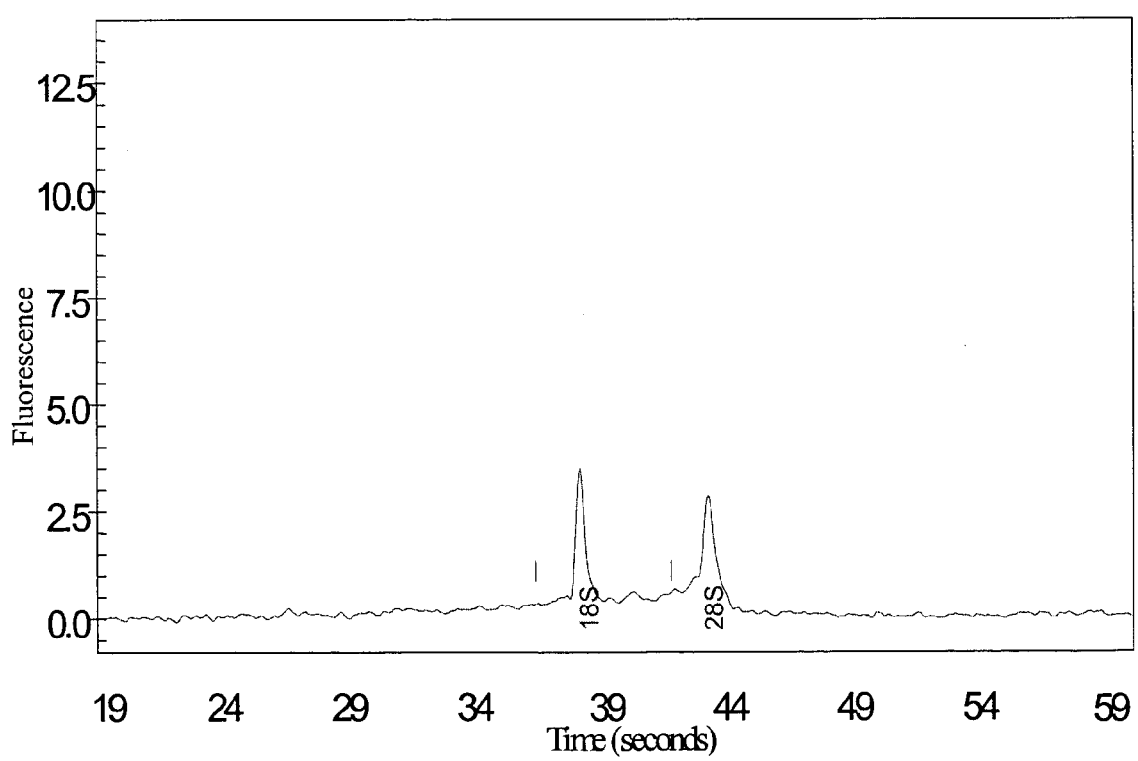

No consistent differences were seen in RNA yield or quality depending on whether phenol-based versus solid phase extraction was used for RNA isolation. Since solid phase extraction is quicker (because the alcohol precipitation steps are avoided), most of the experiments used this method. To optimize RNA isolation using solid-phase extraction, the minimum elution volume needed for complete RNA recovery was tested. It was found that thorough elution of the RNA required at least 40 µL of solution and was improved by performing the elution using sequential 10 µL aliquots and by heating the solution to 95° C. About 65%-75% of the RNA was typically recovered in the first 2×10 µL elution (FIGS. 2A-B). RNA yields were improved by altering the composition of the second wash solution. Based on these results a solid-phase extraction device was designed with a very small filter to permit quantitative recovery of RNA in a small elution volume (about 20 µl).

Figure 3:
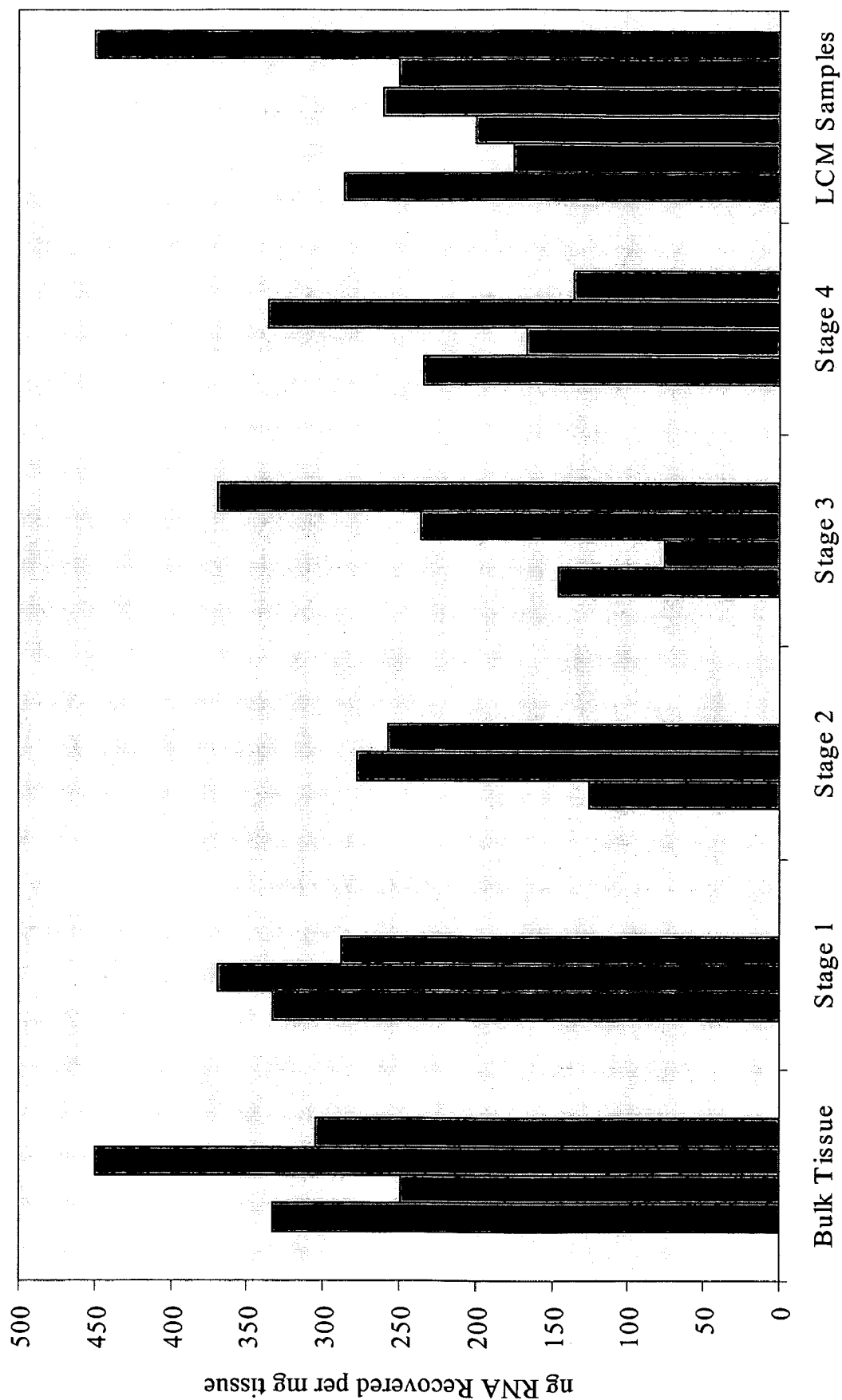
FIG. 3. Yield data for RNA recovered from bulk tissue, from sections at various stages of processing, and after LCM. RNA was isolated directly from slides from replicate mouse brain sections (approximately 1 $cm^2 \times 10$ microns) after each stage of processing, as well as from bulk brain tissue and from LCM-microdissected 1 $mm^2$ samples. RNA was quantified on the Agilent Bioanalyzer. Yields are expressed as ng of total RNA per 1 mg of tissue. One of the data points from the bulk tissue samples was provided by the Harvard Brain Bank, and relates to average yield of RNA from human brain. The four tissue processing stages are described in the text. One source of variation in the replicates prepared from slides is in how thoroughly the tissue lysate was scraped from the slide; this step is problematic and probably accounts for much of the variation.

FIG. 3 shows that the yields of RNA are maintained throughout the all tissue processing stages, as well as during microdissection. Furthermore, these results indicated that the LCM process itself does not result in reduced yields of RNA (FIG. 3). RNA yields per mg are actually slightly higher in LCM samples compared to yields from sections lysed on the slides; this is probably due to more thorough recovery of the sample from the slide using LCM compared to recovering the lysate by pipetting.

Example 6

Comparison of RNA from Section Exposed to Water and Section Not Exposed to Water Staining Protocol Involving Dye Not Dissolved in Water-Containing Solution A tissue section mounted on a slide was fixed in 75% ethanol with 7 dips. The slide was then incubated for 20 seconds in 1% cresyl violet acetate dissolved in 100% EtOH. The dye was made by dissolving solid cresyl violet acetate (Aldrich cat #86,098-0) at a concentration of 1% (w/v) in ACS-grade 100% EtOH at room temperature, covering the mixture with foil, and stirring it with a magnetic stirrer for several hours or overnight. The stain was then filtered through a 0.45 µM filter unit prior to use.

After exposure to the dye, the slide was then gently tapped on an absorbent surface to remove excess stain before placing the slide into the next set of solutions. The slide was then subjected to the following:
1. 75% EtOH for 7 dips;
2. 95% EtOH for 7 dips;
3. 100% EtOH for 30 seconds; excess EtOH removed by gently tapping the slide on absorbent surface;
4. xylene, 5 minutes; and,
5. xylene again, 5 minutes.

The slide was then air-dried for 10 minutes. It was then either dessicated overnight at room temperature or subjected to LCM.

RNA Extraction

Tissue was transferred to solution of approximately 0.1 ml of Lysis Solution sold in the RNAqueous™-Micro Kit from Ambion (Cat #1927). When LCM was not used, lysis solution was pipetted onto the tissue section on the slide and then the lysate was scraped and pipetted up from the slide into a microfuge tube. Additional lysis solution was used to rinse the slide to recover residual sample.

The Lysis Solution contains guanidinium thiocyanate and other components effective for disrupting cell membranes and inactivating cellular nucleases. For tissue sections mounted on glass slides, the Lysis Solution was introduced onto the surface of the tissue section, mixed with a plastic pipette tip, and then aspirated up from the slide and transferred to a microfuge tube. A second aliquot of Lysis Solution was then added to the slide and used to remove all or most residual tissue sample, which was transferred to the same vessel as the initial tissue lysate.

The tissue lysate was mixed with one-half volume of 100% ethanol and then applied to the filter cartridge included in the Ambion RNAqueous™-Micro kit, which is a silica filter. The fluid was passed through the filter by brief centrifugation at approximately 13,000 rpm (about 16,000× g) in a microcentrifuge. The RNA in the tissue lysate bound to the silica filter during this step, while most of the proteins and DNA in the tissue lysate passed through in the filtrate.

The filter was then washed three times by successively applying about 200 µl of Wash Solution #1 from the RNAqueous™-Micro kit, followed by two applications of about 200 µl of Wash Solution #2/3 from the RNAqueous™-Micro kit, to the silica filter and passing the fluid through each time by brief centrifugation as described above. After the third wash step, the filter was centrifuged for 1 minute to remove any residual fluid.

The RNA was then eluted from the silica filter by placing the filter cartridge into a clean microfuge tube and applying an arbitrary volume of water, or preferably of water containing approximately 0.1 mM EDTA (to chelate divalent cations) to the filter and centrifuging the filter for about 1 minute at around 13,000 rpm, which results in transfer of the bound RNA from the silica filter into the collection tube. A typical volume of solution used for elution was 20 µl, applied as successive 10 µl aliquots. The solution used for elution was typically heated to about 70° C. before use.

Some samples were treated with DNase to remove residual contaminating genomic DNA.

Total RNA was extracted from thin tissue sections after staining, in order to compare the extent to which intact RNA is recovered using the two methods. To assess RNA intactness in the tissue prior to processing, RNA was also extracted from a section immediately after sectioning, before any subsequent processing steps were carried out.

Figure 4:
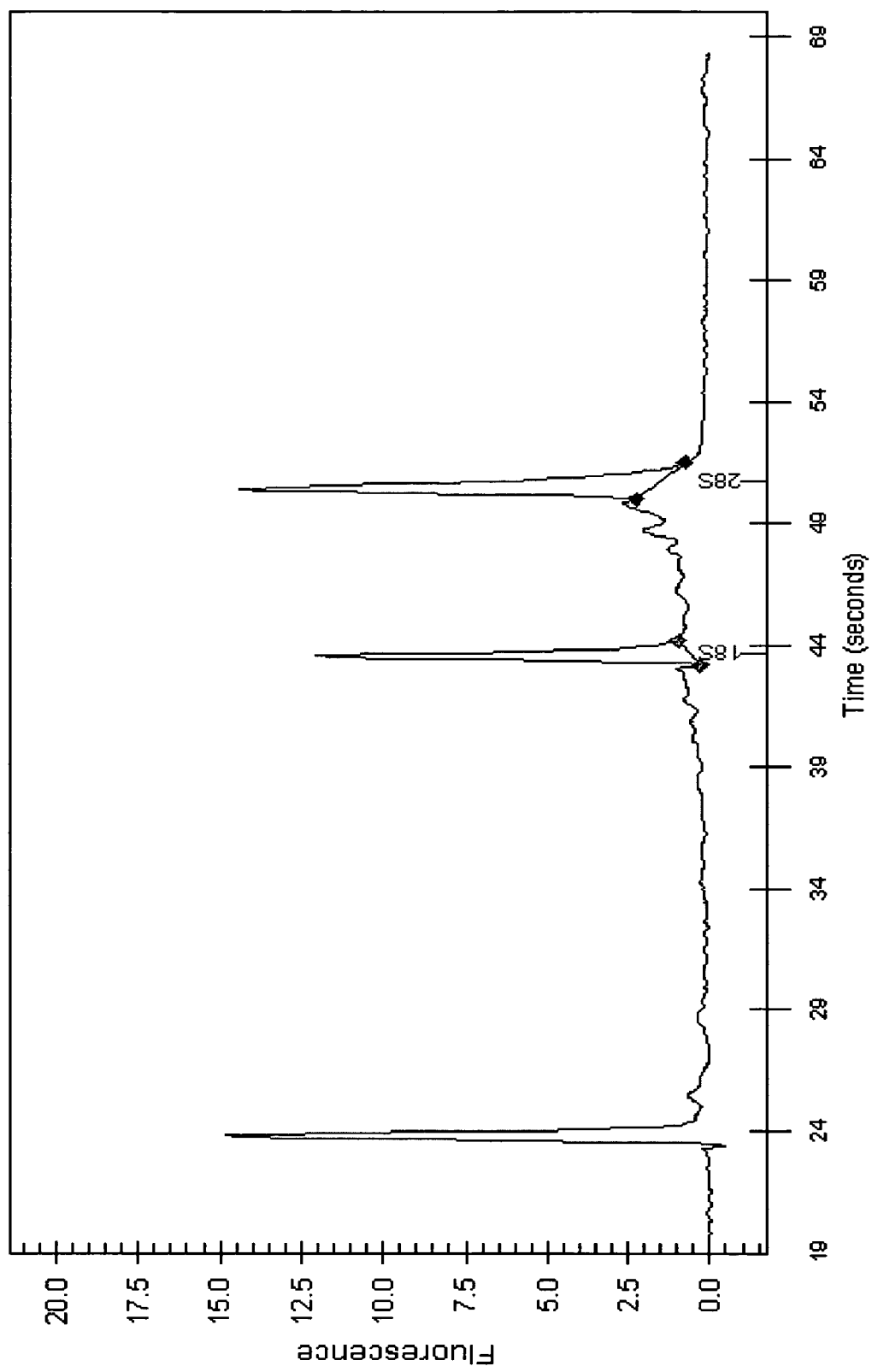
FIG. 4. Recovery of intact RNA from mouse brain tissue sections prior to fixation and staining steps. To assess the RNA intactness in the tissue prior to processing, total RNA was extracted from several thin tissue sections (approximately 10 microns thick) of mouse brain immediately after sectioning, prior to subsequent processing. Tissue sections were processed and RNA isolated using solid-phase extraction onto a silica matrix, as described in the text. The RNA was analyzed by capillary electrophoresis on the Agilent Bioanalyzer. Note the prominent peaks corresponding to 18S rRNA and 28S rRNA, which are indicative of intact total RNA.

A tissue section was obtained from a mouse brain and the RNA was extracted as described above, except RNA was isolated from a section that was not put on a slide and was therefore not processed at all. Instead, the cut section was collected directly from the cryostat blade into a microfuge tube; this was done to verify that the RNA was intact prior to any manipulation of the sample other than freezing and embedding and sectioning. As shown in FIG. 4 intact RNA from the unprocessed section, evidenced by the prominent peaks of 18S and 28S ribosomal RNA, was observed.

A tissue section from a mouse kidney was prepared and stained using a conventional water-based staining method (Kazumori et al, 2001). Specifically, the following steps were employed.
1. pre-staining fixation steps: Tissue sections were adhered to clean glass slides and dipped successively for 30 seconds in 75% ethanol, followed by dipping for 30 seconds in DEPC-treated water.
2. staining step: tissue sections were incubated for 1 minute in 1% cresyl violet acetate dissolved in DEPC-water. Slides were removed and blotted on absorbent paper to remove excess stain.
3. post-staining steps: tissue sections were dipped successively for 30 seconds in each of the following solutions: DEPC water, 70% ethanol, 95% ethanol, 100% ethanol; blotted to remove excess ethanol;
4. sections were then dipped in xylene for 5 minutes, transferred to second xylene solution for 5 minutes, air-dried for 10 minutes Tissue sections were then lysed directly on the slide in 100 microliters per section of guanidinium lysis solution, recovered by pipetting into a microfuge tube, and RNA isolated as described in the text. The RNA was eluted in 15 µl final volume, treated with DNase, and 1 µl of the RNA was analyzed by capillary electrophoresis on the Agilent Bioanalyzer. RNA was recovered from it and analyzed. As is shown in FIG. 5, using the water-based method, degraded RNA was observed, as indicated by the lack of prominent 18S and 28S ribosomal RNA peaks.

Figure 6:
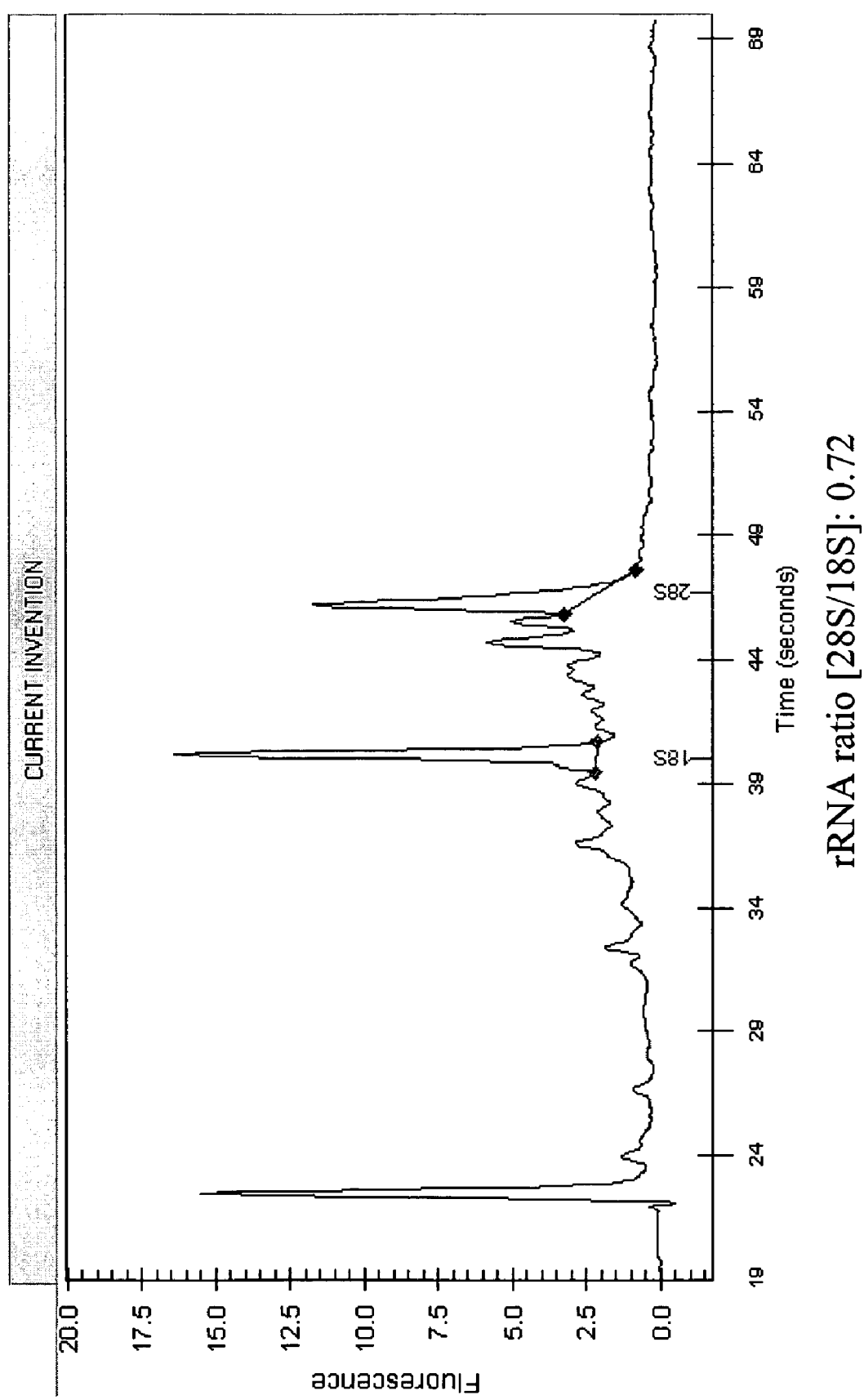
FIG. 6. Recovery of more intact RNA from mouse kidney section processed using the staining method of the current invention. To assess the RNA intactness, tissue sections were processed according to the method of the current invention. 1 µl of the RNA was analyzed by capillary electrophoresis on the Agilent Bioanalyzer. Note that distinct peaks can be seen, corresponding to 18S rRNA and 28S rRNA.

This was in contrast to the quality and quantity of RNA from a tissue section from a mouse kidney that was prepared and stained without exposure to a solution comprising more than 25% water. FIG. 6. For the samples in FIG. 6, total RNA was extracted from three thin sections (10 microns thick) of frozen mouse kidney embedded in OCT, after processing using the following protocol:
1. pre-staining fixation step: Tissue sections were adhered to clean glass slides and dipped seven times in 75% ethanol.
2. staining step: tissue sections were incubated for 20 seconds in 1% cresyl violet acetate dissolved in 100% ethanol. Slides were removed and blotted on absorbent paper to remove excess stain.
3. post-staining steps: tissue sections were dipped successively for 7 dips each time in each of the following solutions: 75% ethanol, 95% ethanol, 100% ethanol; blotted to remove excess ethanol;
4. sections were then dipped in xylene for 5 minutes, transferred to second xylene solution for 5 minutes, air-dried for 10 minutes Tissue sections were then lysed directly on the slide in 100 microliters per section of guanidinium lysis solution, recovered by pipetting into a microfuge tube, and RNA isolated as described above. The RNA was eluted in 15 µL final volume, treated with DNase, and 1 µl of the RNA was analyzed by capillary electrophoresis on the Agilent Bioanalyzer.

Figure 5:
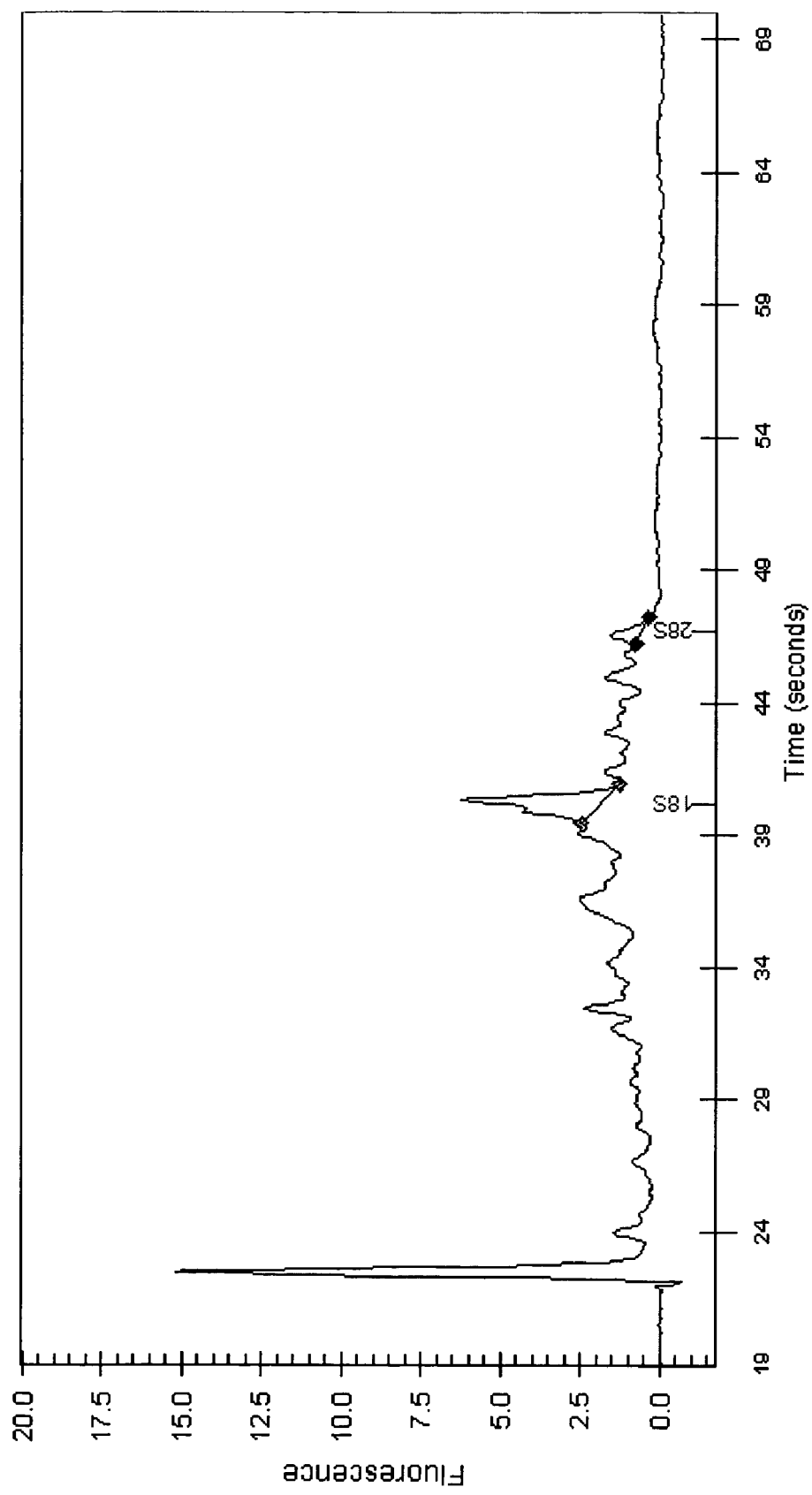
FIG. 5. Recovery of degraded RNA from mouse kidney section processed using conventional water-based staining method. To assess the RNA intactness in tissue sections processed according to standard methods that include exposing the sections to water, total RNA was extracted from three thin sections (10 microns thick) of frozen mouse kidney embedded in OCT. after processing using the protocol described in Kazumori et al., 2001. The RNA was eluted in 15 µL final volume, treated with DNase, and 1 µl of the RNA was analyzed by capillary electrophoresis on the Agilent Bioanalyzer. Note the lack of distinct peaks corresponding to 18S rRNA and 28S rRNA, which is indicative of degraded RNA.

The 18S and 28S ribosomal RNA peaks in FIG. 6 were more prominent in this RNA preparation, compared to the RNA recovered from samples stained using the conventional method, shown in FIG. 5.

Example 7

Comparison of RNA from LCM Sample Exposed to Water and LCM Sample Not Exposed to Water RNA extracted from an LCM sample from a mouse brain tissue section stained using the Conventional Staining Method discussed in Example 1 was compared to RNA extracted from an LCM sample from a mouse brain tissue section stained according to the method of the invention disclosed in Example 6.

A thin section (8 micron) was cut from a frozen OCT embedded mouse brain and adhered to a clean glass slide. Tissue was processed and stained as described in FIG. 5 and its accompanying text. LCM was then carried out on the tissue using the Arcturus Pixcell II workstation, with power setting of 35 mW, pulse duration of 12 msec, and a spot size of 30 µM. Six one square millimeter subregions of the section were recovered on the thermoplastic film and lysed in 100 µl of guanidinium-based lysis solution, and RNA isolated by solid phase extraction onto a silica matrix as described in the text. The RNA was eluted in 15 µL final volume, treated with DNase, and 1 µl of the RNA was analyzed by capillary electrophoresis on the Agilent Bioanalyzer, which is shown in FIG. 7.

Figure 7:
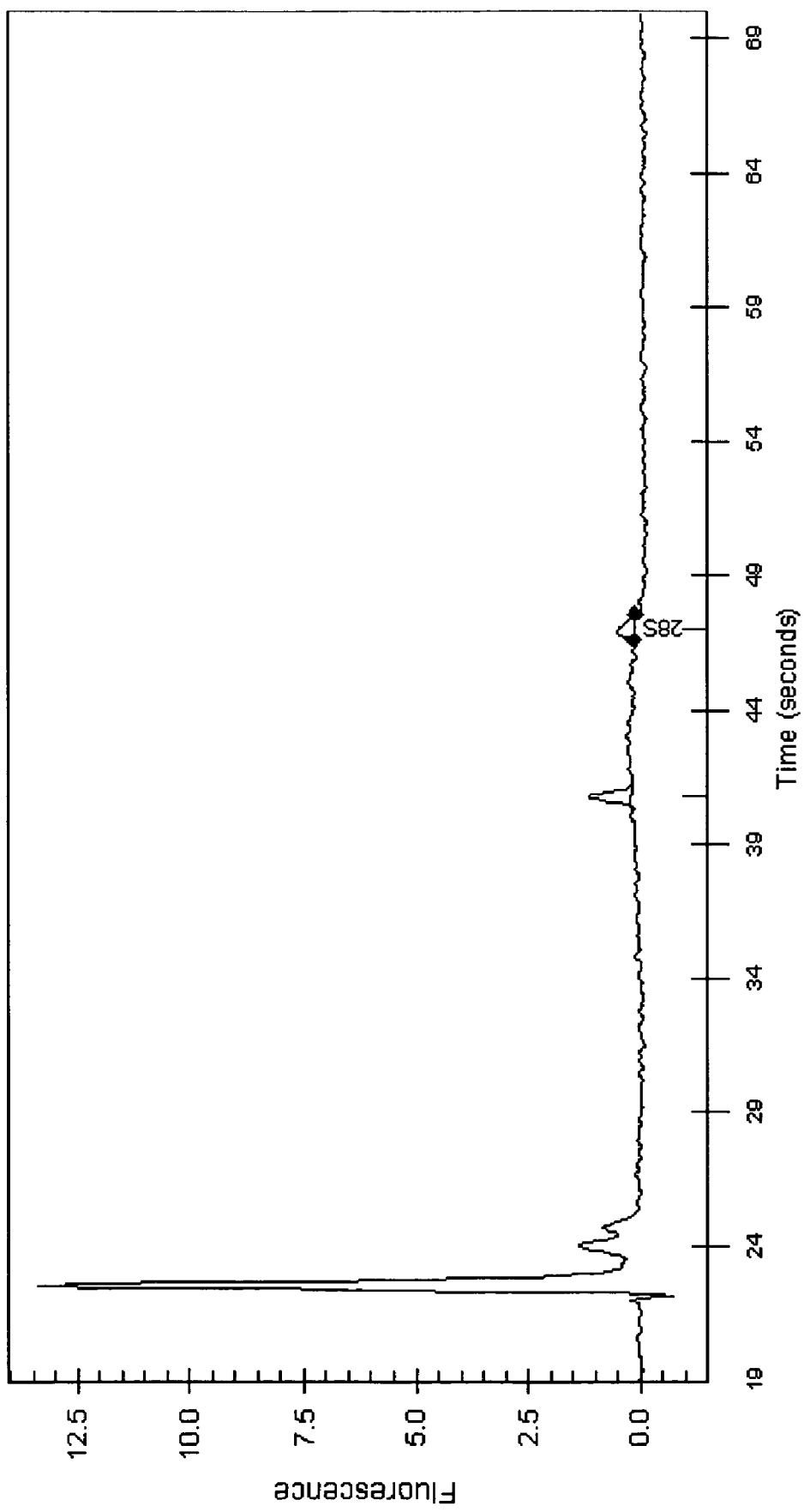
FIG. 7. Recovery of degraded total RNA from LCM microdissected mouse brain section processed using conventional water-based staining method. RNA was isolated from a tissue section prepared by a conventional water-based staining method that was subsequently subject to LCM. RNA was extracted by solid phase extraction onto a silica matrix as described in the text. The RNA was eluted in 15 µL final volume, treated with DNase, and 1 µl of the RNA was analyzed by capillary electrophoresis on the Agilent Bioanalyzer. Note the very low yield and lack of prominent peaks of 18S rRNA and 28S rRNA.

FIG. 7 shows the lack of prominent 18S and 28S ribosomal RNA peaks in RNA preparation from the conventional staining method, which is indicative of degraded RNA.

Figure 8:
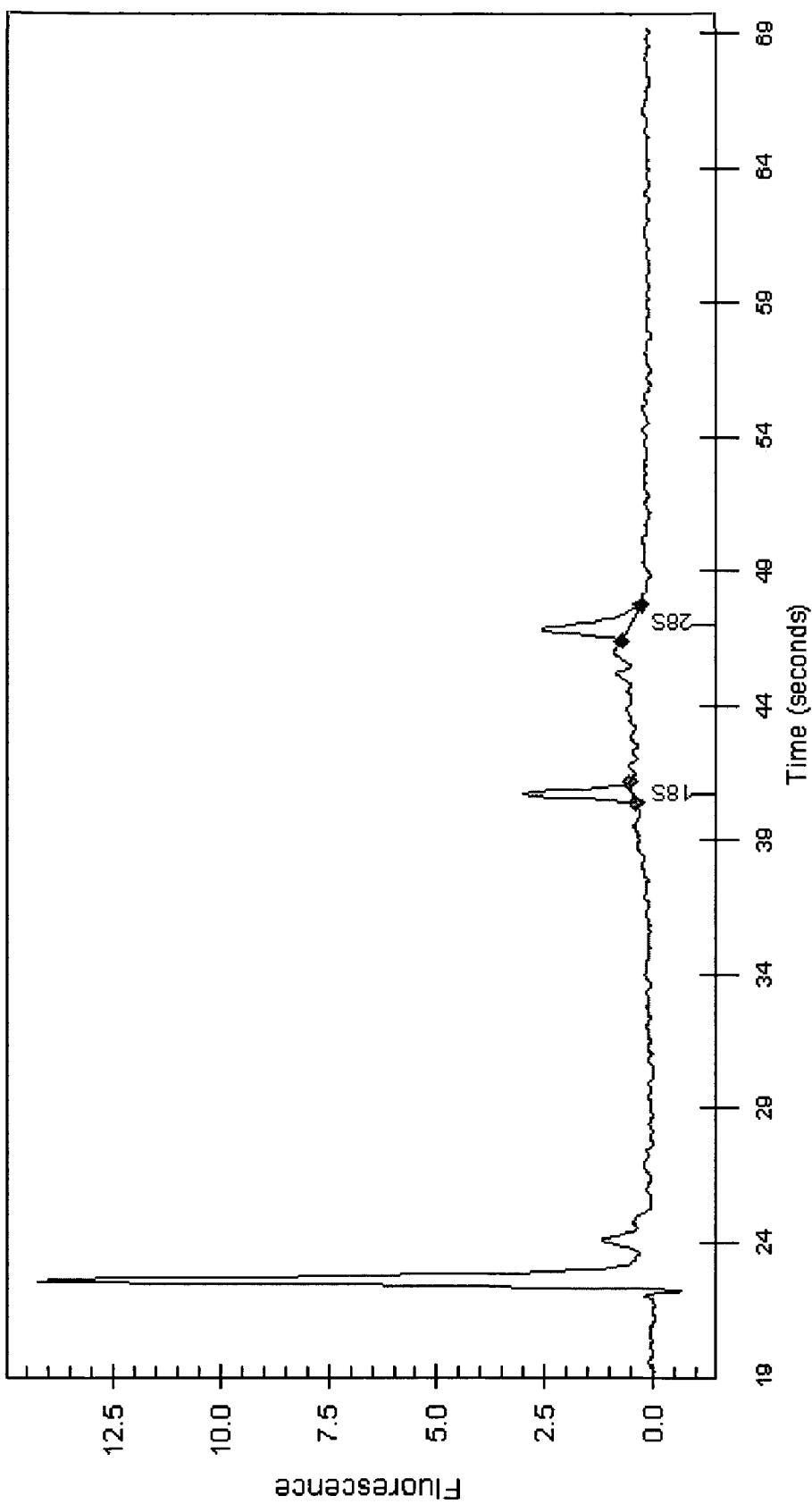
FIG. 8. Recovery of higher yield of more intact total RNA from LCM microdissected mouse brain section processed using staining method of the current invention. RNA was isolated from a tissue section prepared by the staining method of the invention, which was subsequently subject to LCM. RNA was extracted by solid phase extraction onto a silica matrix as described in the text. The RNA was eluted in 15 µl final volume, treated with DNase, and 1 µl of the RNA was analyzed by capillary electrophoresis on the Agilent Bioanalyzer. Note the more prominent 18S rRNA and 28S rRNA peaks in this RNA preparation compared to the RNA recovered from LCM samples shown in FIG. 7.

For FIG. 8, a thin section (8 micron) was cut from a frozen OCT embedded mouse brain and adhered to a clean glass slide. Tissue was processed and stained as described in text Example 6, according to the staining method of the invention. Laser Capture Microdissection (LCM) was then carried out on the tissue using the Arcturus Pixcell II workstation, with power setting of 35 mW, pulse duration of 12 msec, and a spot size of 30 µM. Six one square millimeter subregions of the section were recovered on the thermoplastic film and lysed in 100 µl of guanidinium-based lysis solution, and RNA isolated by solid phase extraction onto a silica matrix as described.

Figure 9:
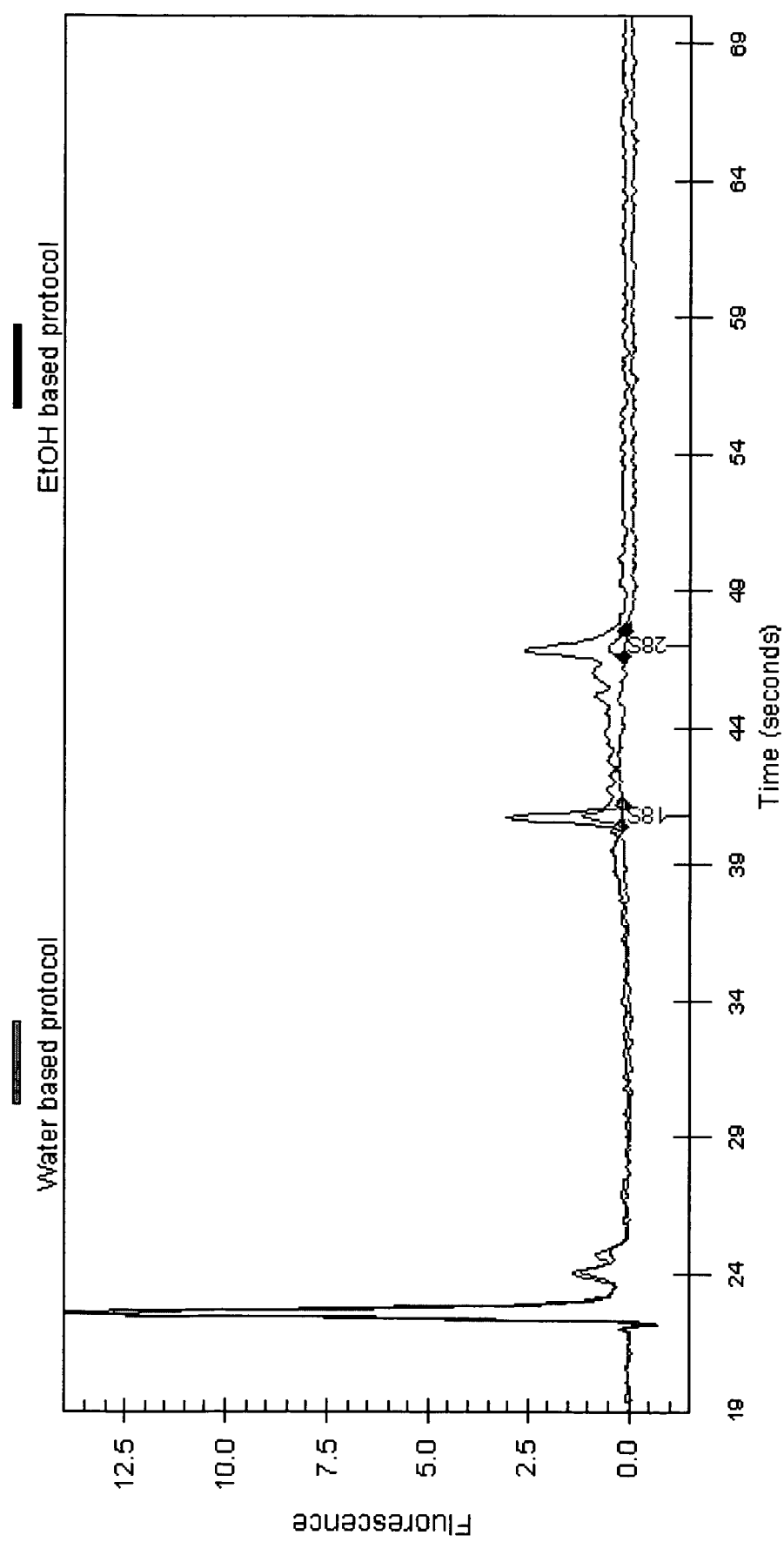
FIG. 9. FIG. shows FIGS. 7 and 8 superimposed on each other to emphasize differences. Lighter line is FIG. 7 while darker line is FIG. 8.

FIG. 8 shows more prominent 18S and 28S ribosomal peaks in this RNA preparation, compared to the RNA recovered from samples stained using the conventional method, shown in FIG. 7. To further assess the differences, FIGS. 7 and 8 were superimposed on one another in FIG. 9. The water-based method is depicted by the lighter line.

Example 8

Sucrose Treatment before Sectioning Improves Morphology of Mouse Brain

Efforts were also focused on improving the ability to distinguish specific subregions of mouse brain. A recent paper relevant to this goal describes the use of sucrose treatment to improve both tissue morphology and recovery of RNA from LCM-dissected samples (Parlato et al., 2002). In this report the tissue (freshly dissected mouse embryos or surgically excised human adenomas) was treated in a solution of 30% sucrose in PBS for several hours at 4° C. before freezing, embedding, and sectioning. The sections were then processed and stained with H&E according to standard methods and used for LCM, and RNA was isolated from the captured cells. These investigators showed that the yield and quality of total RNA recovered from the tissue processed using the sucrose treatment prior to sectioning were significantly better than that of tissue processed according to alternative protocols using alcoholic solvents.

In general the morphology of frozen sections is inferior to that of formalin fixed/paraffin embedded sections. However, the sucrose procedure described by Parlato et al. was used in conjunction with the ethanol staining protocol developed, for processing freshly dissected mouse brain for LCM. Brains were stored in the 30% sucrose solution for 6 hours at 4° C. with intermittent gentle agitation before sectioning. Sections were stained in 1% cresyl violet in 100% ethanol as described above. The sucrose procedure in combination with ethanol-based staining showed improved morphology of mouse brain sections, compared to samples stained in the same way, but processed without prior sucrose incubation. Moreover, the RNA recovered from LCM-captured tissue samples processed using the sucrose pre-sectioning procedure followed by staining in ethanol is substantially intact, as shown by Agilent analysis.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references are specifically incorporated herein by reference.

U.S. Pat. No. 5,614,376
U.S. Pat. No. 6,316,234
U.S. Patent Application No. 20030064518
U.S. Patent Publication No. 20020006625
U.S. Patent Publication No. 20020132222
Ambion TechNotes, vol. 9, no. 6, "Working with Laser Capture Microdissection Samples," on the internet at ambion.com/techlib/tn/96/9616.html.
Ambion TechNotes, "Staining Protocol for LCM Samples," on the internet at ambion.com/techlib/misc/LCM_staining.html.
Ambion, Inc., RNAqueous™-Micro Instruction Manual, Version 0303 (Cat #1927).
Arcturus, HistoGene™ LCM Frozen Section Staining Kit, Version A (Cat #KIT0401).
Bakay et al., *BMC Bioinformatics* 3:4, 2002.
Bonner et al., *Science* 278:1481, 1997.
Carmichael et al., *Methods in Enzymology* 65:380-391, 1980.
Danielson et al., *Genomics* 3:454, 1994.
Eberwine et al. *PNAS* 89:3010, 1992.
Fawcett et al., *A textbook of histology*, 12th edition, New York: Chapman & Hall, 1994.
Fend et al., *American Journal of Pathology* 154(1):61, 1999.
Fend et al., *Pathobiology* 68:209-214, 2000.
Fend et al, *Pathobiology* 68:209, 2001.
Fink et al., *American Journal of Pathology* 157(5):1459, 2000.
Fink et al., *Laboratory Investigation* 80(3):327, 2000.
Goldworthy et al., *Molecular Carcinogenesis* 25:86, 1999.
Green, Floyd J., The Sigma Aldrich Handbook of Stains, Dyes, and Indicators, Aldrich Chemical Company, Inc., Milwaukee, Wis., 1990.
Hayes et al *Br. J Cancer* 83:1154-1160, 2000.
Hegde et al., *BioTechniques* 29:548, 2000.
Karpuj et al., *Nature Medicine* 8:143, 2002.
Kazumori et al., *FEBS Letters* 489:208, 2001.
Kitahara et al., *Cancer Research* 61:3544, 2001.
Kohda et al., *Kidney International* 57:321-331, 2000.
Leeson et al., *Atlas of Histology*, Philadelphia:Saunders, 1988.
Leethanakul et al., *Oral Oncology* 36:474, 2000.
Lindeman et al., *Diagnostic Molecular Pathology* 11(4): 187-192, 2002.
Luo et al., *Nature Medicine* 5:117, 1999.
Luzzi et al., *Am J Pathology* 158:2005, 2001.
Mackler et al., *Molecular Pharmacology* 44:308, 1993.
Murakami et al., *Kidney Int.* 58:1346, 2000.
Ohyama et al., *BioTechniques* 29:530, 2000.
Oliva et al., *J Neuroscience* 20:3354, 2000.
Pabon et al., *BioTechniques* 31:874, 2001.
Pak et al., *PNAS* 97:11232, 2000.
Parlato et al., *Anal. Biochem.* 300:139, 2002.
Patel et al., *Crit Rev Oral Biol Med* 12:55, 2001.
Rogers, *Cells and tissues: an introduction to histology and cell biology*, London; New York:Academic Press, 1983.
Suarez-Quian et al., *BioTechniques* 26:328, 1999.
Sugiyama et al., *Am J Clin Pathol* 2002 January; 117(1): 109-16
Tanji et al., *Experimental Nephrology* 9:229, 2001.
Trogan et al., *PNAS* 99(4):2234-2239, 2002.
Van Gelder et al., *PNAS* 87:1663, 1990.
Vincent et al., *Journal of Neuroscience Research* 69:578-586, 2002.
Wang et al., *Nature Biotechnology* 4:457, 2000.
Wodicka et al., *Nature Biotechnology* 15:1359, 1997.
Wong et al., *PNAS* 97:12601, 2000.
Zhao et al., *Genes and Dev.* 14:981, 2000.
Zhou et al, *Bioc. Biophys. Res Comm* 266:556, 1999.

What is claimed is:

1. A method for extracting nucleic acid molecules from a tissue section comprising:
   a) contacting a tissue section with a first set of one or more solutions comprising no more than about 50% water;
   b) contacting the tissue section with one or more stain in a solution comprising no more than about 50% water;
   c) contacting the tissue section with a second set of one or more solutions comprising no more than about 50% water; and
   d) then extracting nucleic acid molecules from the tissue section.

2. The method of claim 1, wherein the stain is in a solution with less than about 10% water.

3. The method of claim 1, wherein one or more of the solutions is at least about 70% alcohol.

4. The method of claim 3, wherein one or more of the solutions is at least about 90% alcohol.

5. The method of claim 4, wherein one or more of the solutions is about 100% alcohol.

6. The method of claim 3, wherein the stain is in a solution that is at least about 80% alcohol.

7. The method of claim 6, wherein the stain is in a solution that is about 100% alcohol.

8. The method of claim 3, wherein the alcohol in at least one of the solutions comprises an alcohol selected from the group consisting of ethanol, methanol, and propanol.

9. The method of claim 1, wherein solutions comprising water include water that has been treated with diethyl pyrocarbonate (DEPC).

10. The method of claim 1, wherein at least one of the solutions in the second set comprises a non-alcohol organic solvent.

11. The method of claim 10, wherein the organic solvent solution is at least about 50% organic solvent.

12. The method of claim 11, wherein the organic solvent solution is at least about 75% organic solvent.

13. The method of claim 12, wherein the organic solvent solution is at least about 90% organic solvent.

14. The method of claim 13, wherein the organic solvent solution is about 100% organic solvent.

15. The method of claim 10, wherein the organic solvent is a hydrocarbon selected from the group consisting of xylene or toluene.

16. The method of claim 1, wherein the stain is selected from the group consisting of cresyl violet acetate, hematoxylin, and eosin.

17. The method of claim 1, wherein the tissue sample is exposed to more than one stain.

18. The method of claim 1, further comprising performing laser capture microscopy on the tissue section before step (a) or before step (d).

19. The method of claim 18, further comprising extracting nucleic acid molecules from cells of the tissue section that have been subjected to laser capture microdissection.

20. The method of claim 19, wherein the nucleic acid molecules include ribonucleic acids (RNA).

21. The method of claim 19, wherein the nucleic acid molecules include RNA.

* * * * *